US009640218B2

(12) United States Patent
Shoemaker et al.

(10) Patent No.: US 9,640,218 B2
(45) Date of Patent: May 2, 2017

(54) PHYSIOLOGICAL CUE PROCESSING

(71) Applicant: Intel Corporation, Santa Clara, CA (US)

(72) Inventors: Garth Shoemaker, Sunnyvale, CA (US); Jonathan Thompson, Santa Clara, CA (US)

(73) Assignee: Intel Corporation, Santa Clara, CA (US)

( * ) Notice: Subject to any disclaimer, the term of this patent is extended or adjusted under 35 U.S.C. 154(b) by 1015 days.

(21) Appl. No.: 13/707,697

(22) Filed: Dec. 7, 2012

(65) Prior Publication Data
US 2014/0161421 A1 Jun. 12, 2014

(51) Int. Cl.
G06K 9/00 (2006.01)
G11B 27/028 (2006.01)
(Continued)

(52) U.S. Cl.
CPC ........... G11B 27/028 (2013.01); G06T 5/002 (2013.01); G06T 5/50 (2013.01); G06T 7/0016 (2013.01);
(Continued)

(58) Field of Classification Search
CPC . A61B 2576/00; A61B 5/0075; A61B 5/0077; A61B 5/0205; A61B 5/1032;
(Continued)

(56) References Cited

U.S. PATENT DOCUMENTS 9,186,111 B2 * 11/2015 Jeanne ................. A61B 6/5288
2006/0189879 A1 8/2006 Miyajima et al.
(Continued)

FOREIGN PATENT DOCUMENTS

CN 101006915 A 8/2007
CN 101198277 A 6/2008
(Continued)

OTHER PUBLICATIONS

International Search Report and Written Opinion received for International Application No. PCT/US2013/073719, mailed Mar. 19, 2014, 19 pages.

(Continued)

Primary Examiner — Tom Y Lu
(74) Attorney, Agent, or Firm — Barnes & Thornburg LLP

(57) ABSTRACT

Physiological cues, such as elevated heart or respiratory rates can be masked from video of a person before the video is sent to another party. The masking of human-perceptible and non-human-perceptible physiological cues removes information from the video that another party could use to determine the person's emotional state. For example, variations in a person's skin color that are typically imperceptible to the human eye and from which a person's heart rate can be detected, can be removed or altered so that another party viewing the video cannot determine the person's actual heart rate in an attempt to determine the person's emotional state, even if they are performing computer analysis on the video. The presence of some physiological cues can be determined by detecting that a physiological measure is above a specified physiological measure threshold. Modified video can have the characteristic that physiological cues are substantially absent in the modified video or that physiological measures extracted from the modified video have a value below an associated physiological measure threshold.

24 Claims, 12 Drawing Sheets

(51) Int. Cl.
*G11B 27/034* (2006.01)
*G11B 27/28* (2006.01)
*G06T 7/00* (2017.01)
*G06T 5/50* (2006.01)
*G06T 5/00* (2006.01)
*A61B 5/024* (2006.01)
*A61B 5/08* (2006.01)
*A61B 5/16* (2006.01)

(52) U.S. Cl.
CPC ............ *G11B 27/034* (2013.01); *G11B 27/28* (2013.01); *A61B 5/024* (2013.01); *A61B 5/0806* (2013.01); *A61B 5/165* (2013.01); *G06F 2203/011* (2013.01); *G06K 9/00315* (2013.01); *G06T 2207/20182* (2013.01); *G06T 2207/30076* (2013.01)

(58) Field of Classification Search
CPC ... A61B 5/4857; A61B 5/7228; A61B 5/7278; A61B 6/5288; G06K 9/00503
See application file for complete search history.

(56) References Cited

U.S. PATENT DOCUMENTS

| | | | |
|---|---|---|---|
| 2007/0027368 A1* | 2/2007 | Collins | A61B 3/0041 600/300 |
| 2007/0230794 A1 | 10/2007 | McAlpine et al. | |
| 2008/0068397 A1 | 3/2008 | Carey et al. | |
| 2008/0294012 A1 | 11/2008 | Kurtz et al. | |
| 2009/0112694 A1 | 4/2009 | Jung et al. | |
| 2009/0133047 A1 | 5/2009 | Lee et al. | |
| 2010/0131878 A1 | 5/2010 | Fujioka | |
| 2011/0166937 A1 | 7/2011 | Bangera et al. | |
| 2011/0251493 A1 | 10/2011 | Poh et al. | |
| 2012/0083675 A1 | 4/2012 | el Kaliouby et al. | |

FOREIGN PATENT DOCUMENTS

| | | | |
|---|---|---|---|
| JP | 2005-218507 A | 8/2005 | |
| JP | 2008-063582 A | 3/2008 | |
| JP | 2008-071341 A | 3/2008 | |
| KR | 2008-063582 | 3/1996 | |
| KR | 2008-218507 | 8/2005 | |
| KR | 2008-71341 | 3/2008 | |
| KR | 100886489 B1 | 3/2009 | |
| WO | 2007/124126 A2 | 11/2007 | |
| WO | 2008004813 A1 | 1/2008 | |
| WO | 2011/127487 A2 | 10/2011 | |
| WO | 2012/066454 A1 | 5/2012 | |
| WO | WO 2012066454 * | 5/2012 | ............... A61B 6/00 |
| WO | 2014089515 A1 | 6/2014 | |

OTHER PUBLICATIONS

Wu et al., "Eulerian Video Magnification for Revealing Subtle Changes in the World," ACM Transactions on Graphics (TOG)—SIGGRAPH 2012 Conference Proceedings, vol. 31, Issue 4, Jul. 2012, 8 pages.
Liu et al., "Motion magnification," ACM Transactions on Graphics (TOG)—SIGGRAPH 2005 Conference Proceedings, vol. 24, Issue 3, Jul. 2005, 8 pages.
Notice of Preliminary Rejection for Korean Patent Application No. 10-2015-7009961, dated Mar. 22, 2016, 6 pages.
Chinese Office Action and English Translation for Application No. 201380058375.7, dated Sep. 14, 2016, 30 pages.
European Search Report for Application No. 13860222.2-1906/2929477, dated Sep. 23, 2016, 9 pages.
Mallick, Satya P., "Specularity Removal in Images and Videos: A PDE Approach," Computer Vision—ECCV 2006, 9th European Conference on Computer Visiona, Graz, Austria, Jan. 1, 2006.
Notice of Final Rejection for Korean Patent Application No. 9-5-2016-078327202, dated Oct. 31, 2016, 3 pages.

* cited by examiner

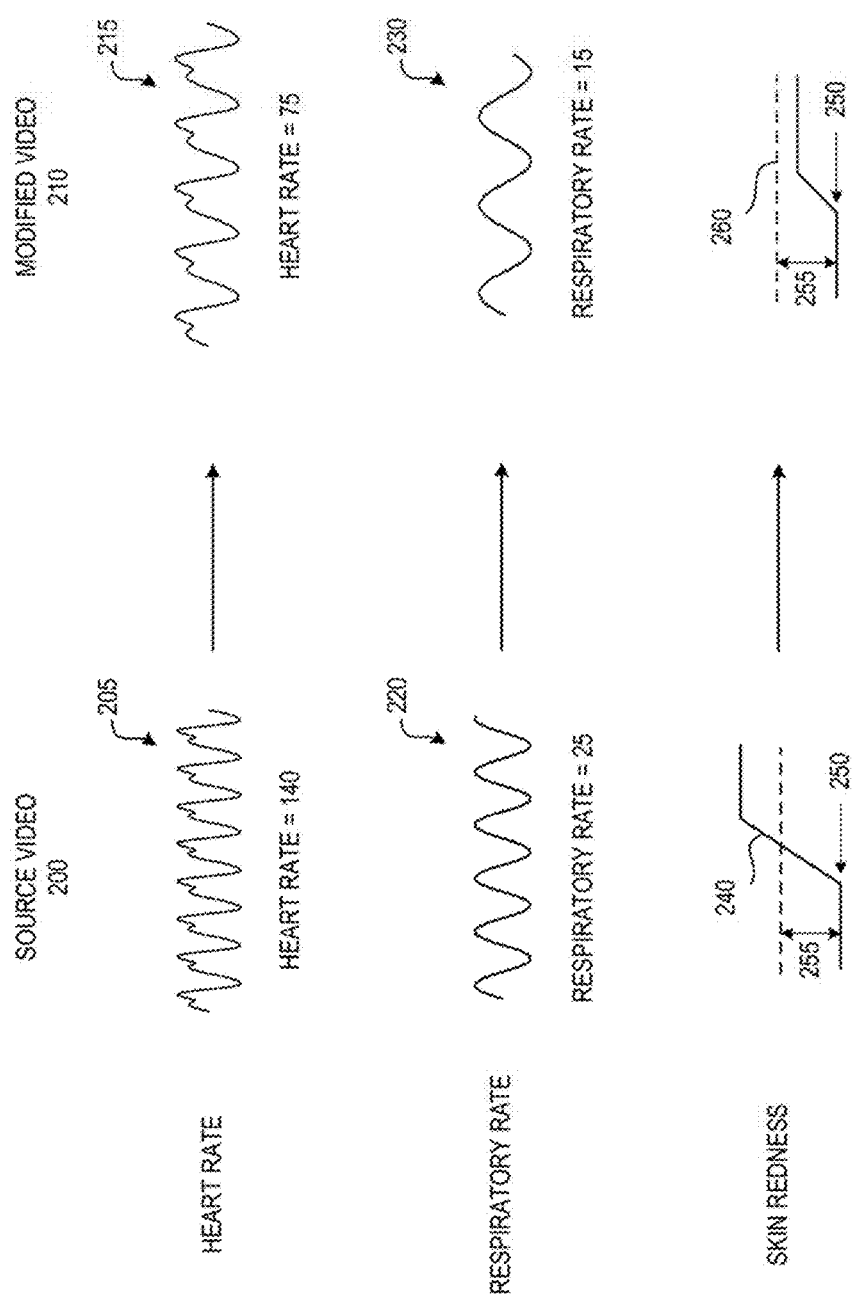

- RECEIVE SOURCE VIDEO OF AT LEAST ONE PERSON COMPRISING ONE OR MORE PHYSIOLOGICAL CUES  
  810
- GENERATE MODIFIED VIDEO IN WHICH AT LEAST ONE PHYSIOLOGICAL CUE IS MASKED  
  820
- SEND MODIFIED VIDEO TO SECOND COMPUTING DEVICE  
  830

- RECEIVE A COMPUTER GRAPHICS MODEL OF A HUMAN CHARACTER COMPRISING A FACE REGION  
  1110
- ADD SKIN TEXTURE COMPRISING A PULSATION EFFECT TO FACE REGION  
  1120

PHYSIOLOGICAL CUE PROCESSING

BACKGROUND

Certain physiological measures, such as heart rate and respiratory rate, can provide insight into a person's emotional state. For example, that a person has an elevated heart rate can suggest that the person is excited or distressed. Thus, characteristics of physiological measures can act as physiological cues indicating a person's emotional state.

A person's heart rate and respiratory rate can be determined in contactless fashion using a camera and a computing device. For instance, a person's heart rate can be determined by taking advantage of the blood pulsation effect—small fluctuations in average skin color intensity that occur as blood passes through capillaries close to the skin surface as the person's heart beats. The blood pulsation effect exists because of how light interacts with human skin. Ambient light is reflected or absorbed by human skin in varying amounts due to the presence of three pigments—melanin, carotene and hemoglobin. The amounts of melanin and carotene in skin typically do not vary over the course of a typical sampling timeframe, but the amount of hemoglobin does varies with the action of blood pulsing into and out of the skin, creating a detectable wave in the average color output of a captured area of the face.

These skin color fluctuations are minute and have been measured at about +/−1% of the average unmodulated skin color intensity. The skin color fluctuations are present in all color channels of a video recording of a person and in the red-green-blue (RGB) color space, the effect is more pronounced in the green channel. In the YCbCr color space (a luminance-chroma color space), the effect is most pronounced in the Y (luminance) channel, with a matching lower-amplitude fluctuation in the Cr channel, one of the chroma channels.

A person's respiratory rate can be determined by detecting the rate at which a person's shoulders and/or chest rises and falls in a video.

BRIEF DESCRIPTION OF THE DRAWINGS

FIG. 2 illustrates exemplary maskings of an elevated heart rate, an elevated respiratory rate and a shift in the redness of a person's face.

FIG. 8 is a flowchart of a first exemplary method of masking physiological cues.

FIG. 11 is a flowchart of an exemplary method of adding a blood pulsation effect to a computer graphics model of a human character.

DETAILED DESCRIPTION

Disclosed herein are technologies that can mask physiological cues that can provide information about a person's emotional state from a video of the person. For example, the disclosed technologies can modify video of a person to mask a person's elevated heart rate, elevated respiratory rate, reddening of the face, nervous tics and other facial or body movements, or physiological responses. A person may exhibit these movements or responses because of being, for example, angry, nervous, distressed or excited. The masking of physiological cues can be useful in situations where a person does not wish video of him or her to reveal information about his or her emotional state, such as persons who are participating in sensitive business negotiations via videoconferencing. Some physiological cues, such as reddening of the face and nervous tics, are perceptible to humans, while others, such as an elevated heart rate as manifested by the blood pulsation effect, are generally not human-perceptible. Parties to a videoconference can employ technologies to detect imperceptible physiological cues of other videoconference participants in an attempt to determine another participant's emotional state. The technologies described herein can act as a countermeasure to such efforts by concealing physiological cues from computer algorithms and humans.

Figure 1:
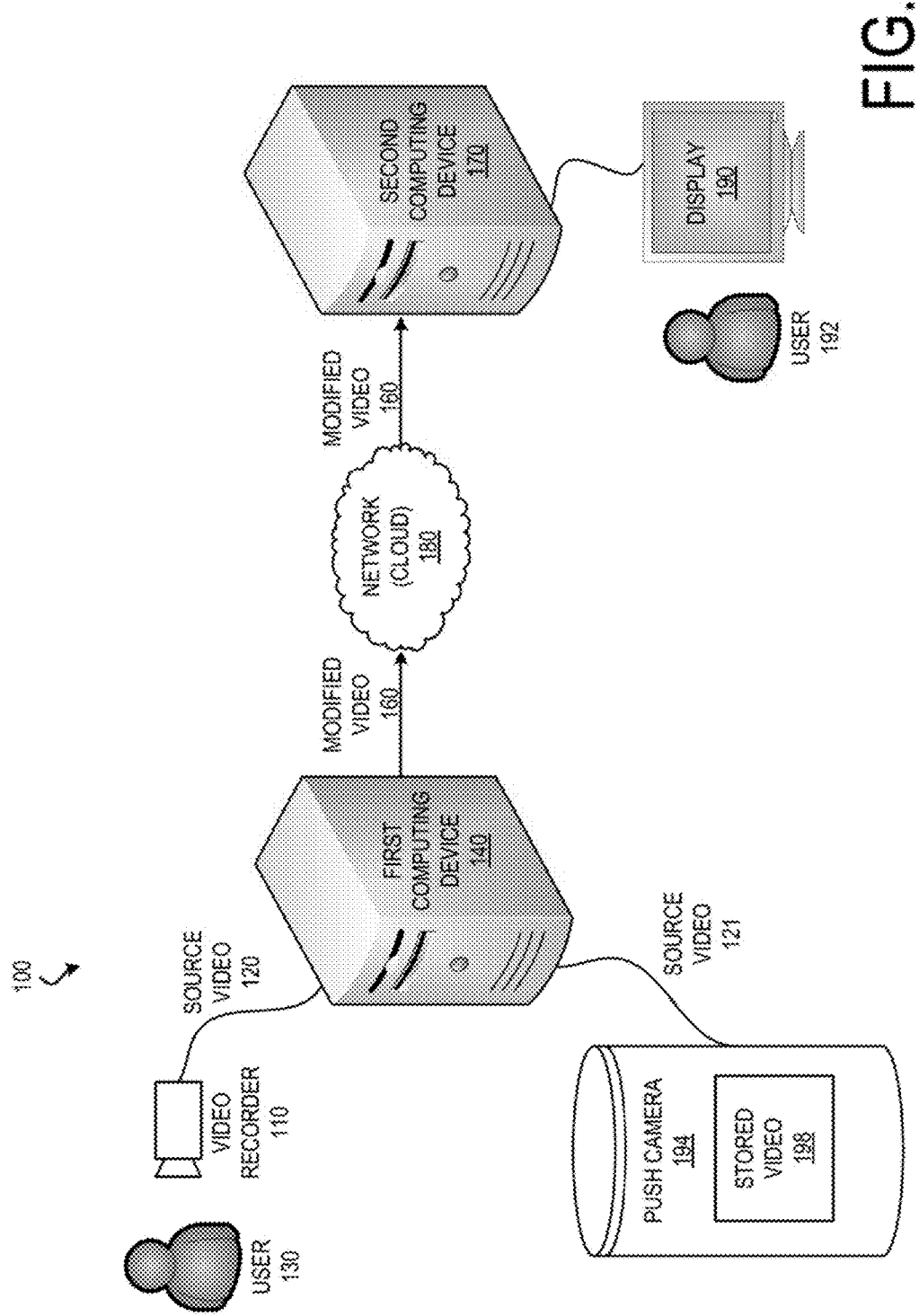
FIG. 1 is a diagram of an exemplary environment in which technologies described herein can be implemented.

Reference is now made to the drawings, wherein like reference numerals are used to refer to like elements throughout. FIG. 1 is a diagram of an exemplary environment 100 in which technologies described herein can be implemented. The environment 100 comprises a video recorder 110 that delivers source video 120 of a person 130 to a first computing device 140. The video recorder 110 can be any device that captures video, such as a smartphone, tablet computer or camcorder. The first computing device 140 modifies the source video 120 to generate a modified video 160 in which physiological cues of the person 130 present in the source video 120 are substantially absent. The modified video 160 is sent to a second computing device 170 via a network or cloud 180 and displayed at a display 190 coupled to the second computing device 170 for viewing by a person 192. The network 180 can be any type of network such as a Local Area Network (LAN), Wide Area Network (WAN) or the Internet. The first and second computing devices 140 and 170 can be any computing device as described herein, such as a mobile device (e.g., smartphone, laptop or tablet computer), desktop computer or server.

The environment 100 further comprises a push camera 194 that stores video data 198 and can deliver stored video data 198 to the first computing device as additional source video 121. The push camera 194 can be any kind of storage media, device or system, such as a video store integrated into the first computing device, such as a hard drive incorporated into a desktop computer, or an external storage device or system, such as an external hard drive or cloud-based storage. Source video, modified video and any other video described herein can be in any video format.

The first computing device 140 can process the source video 120 to mask physiological cues that can provide information about the emotional state of the person 130. As used herein, the term "physiological cues" means a person's bodily or facial movements or physiological responses that indicate or suggest the person's emotional state. Examples of physiological cues include elevated heart rate, elevated respiratory rate, reddening of a person's face, nervous tics (e.g., blinking) and brief, involuntary micro expressions. A person can have an elevated heart or respiratory rate in response to being excited or nervous, a reddened face in response to being angry or embarrassed, or have a nervous tic (such as rapid blinking or a twitch at the corner of the mouth) that manifests itself when they are nervous. The presence of some physiological cues can be detected based on physiological measures determined from video of a person. As used herein, the term "physiological measure" is a measurement of a physical characteristic of a person, such as their heart rate, respiratory rate and the redness of their face. People can exhibit physiological cues other than those listed above, and the technologies described herein can be used to mask these additional physiological cues.

In some embodiments, the masking of physiological cues in a source video comprises determining a physiological measure from the source video, determining from the physiological measure that the video contains a physiological cue, and generating modified video in which the physiological cue is substantially absent. In various embodiments, determining from the physiological measure that the video contains a physiological cue comprises determining that the physiological measure exceeds an associated physiological measure threshold, such as a heart rate threshold or a respiratory threshold.

FIG. 2 illustrates exemplary maskings of an elevated heart rate, an elevated respiratory rate and reddening of a person's face present in a source video 200. A signal 205 corresponding to a person's heart rate can be extracted from the source video 200 by, for example, measuring the blood pulsation effect—small fluctuations in the average skin color of a person as blood passes through capillaries close to the skin. The measure 205 indicates that the person has a heart rate of 140 beats per minutes (bpm). The measure 205 can be determined to be a physiological cue indicating that the person is excited or agitated as the heart rate of 140 bpm exceeds a heart rate threshold of, for example, 90 bpm indicating that a person is in an excited state. The elevated heart rate physiological cue can be masked by modifying the source video to generate a modified video 210 in which the blood pulsation effect is modified to indicate a heart rate at or below the heart rate threshold. For example, measuring the fluctuations in the average skin color of a person in the modified video 210 to measure the person's heart rate can yield a signal 215 corresponding to a heart rate of 75 beats per minute, a value below the heart rate threshold and indicating that the person is in a calm state. Alternatively, the elevated heart rate physiological cue can be masked by generating a modified video in which color fluctuations in the person's face due to the blood pulsation effect are substantially absent.

An elevated respiratory rate can be masked in a similar fashion. A signal 220 corresponding to a person's respiratory rate can be extracted from the source video 200 by, for example, measuring the rate at which the person's chest and/or shoulders rise and fall in the source video 200). The measure 220 indicates that the person has a respiratory rate of 25 breaths per minute, which can be determined to be a physiological cue indicating that the person is excited as it exceeds a respiratory rate threshold of, for example, 20 breaths per minute. The elevated respiratory rate physiological cue can be masked by modifying the source video 200 to generate the modified video 210 in which the shoulders and/or chest of the person rise and fall at a rate below the respiratory rate threshold. For example, measuring the chest or shoulder rise and fall rate in the modified video 210 to measure the person's respiratory rate can yield a signal 230 corresponding to a respiratory rate of 15 beats per minute, a value below the respiratory rate threshold of 20 beats per minute and indicating that the person is in a calm state. Alternatively, the elevated respiratory rate physiological cue can be masked by generating a modified video in which the rise and fall rate of the person's chest due to breathing has been substantially removed.

The reddening of a person's face can also be masked using techniques described herein. A signal 240 corresponding to a person's skin redness can be extracted from the source video 200 by, for example, determining the color of a person's face. The measured skin redness can be determined to be a physiological cue indicating that the person is angry, upset or embarrassed if the redness of the person's face has shifted from a skin redness baseline 250 by more than a skin redness shift threshold 255. The skin redness physiological cue can be masked by modifying the source video 200 to generate the modified video 210 in which the redness of the person's face is within the skin redness shift threshold of the skin redness baseline. For example, measuring the redness of the person's face in the modified video 210 can yield a signal 260 corresponding to a skin redness that is within the skin redness shift threshold 255 of the redness baseline 250.

Figure 3A:
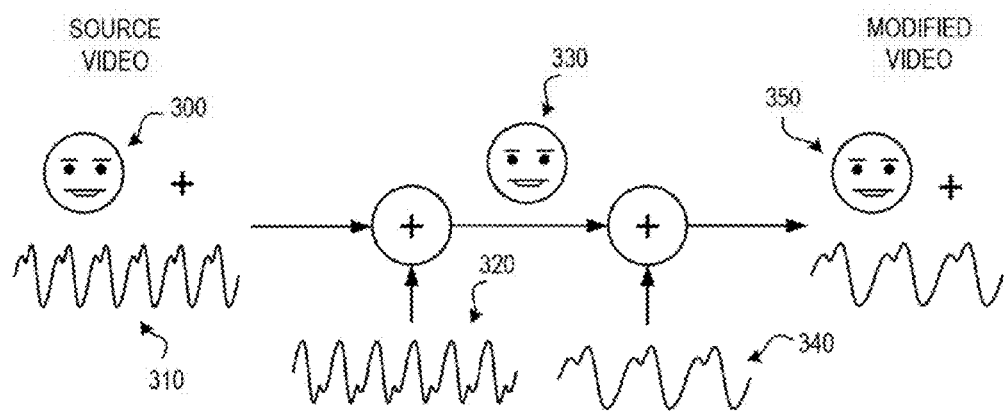
FIGS. 3A-3C illustrate additional exemplary maskings of physiological cues.
Figure 3B:
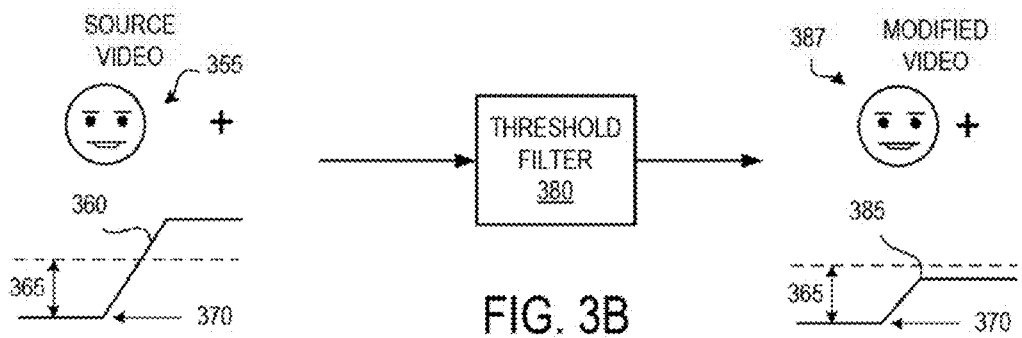
Figure 3C:
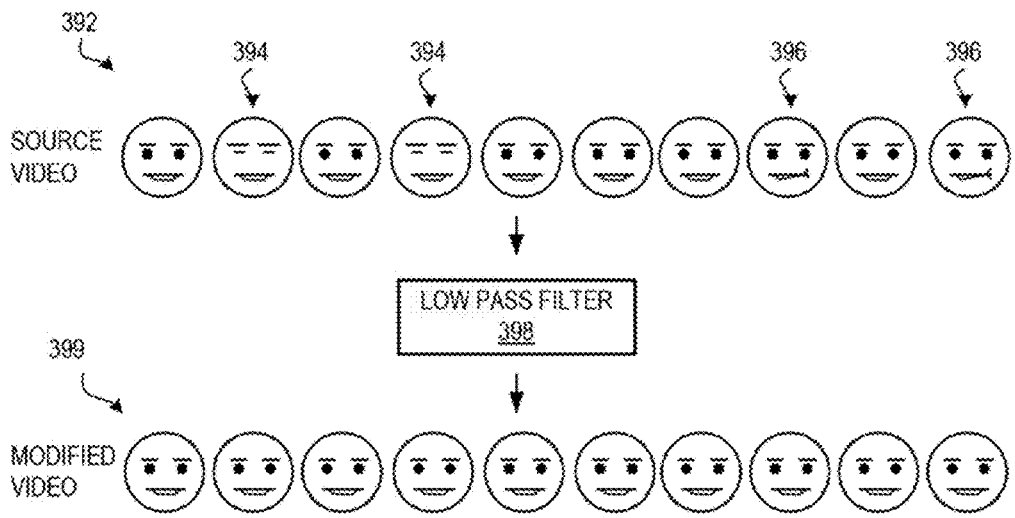

FIGS. 3A-3C illustrate additional exemplary maskings of physiological cues. FIG. 3A shows an exemplary masking of a physiological cue by canceling the component of the source video that allows detection of the physiological cue, and adding a component to the modified video that yields a physiological measure that does not indicate the presence of a physiological cue. In FIG. 3A, the source video comprises video of a person 300 comprising bodily or facial movements or other physiological response from which a signal 310 corresponding to a physiological measure can be extracted. If the physiological measure exceeds a corresponding threshold (e.g., an extracted heart rate exceeds a heart rate threshold), a signal 320 is generated such that adding the signal 320 to the source video 300 results in an intermediate video 330 in which the bodily or facial or other physiological response has been removed. For example, if the source video comprises skin color fluctuations due to the blood pulsation effect, the video signal 320 can comprise skin color fluctuations that cancel the blood pulsation effect in the source video 300. Thus, addition of the video signal 320 to the source video 300 yields an intermediate video 330 in which the skin color fluctuations in the person's face have been substantially removed. Similarly, if the source video 300 comprises fluctuations in the outline of a person's shoulders from which a respiratory rate can be extracted, the video signal 320 can comprise a signal that removes the rise and fall of the shoulders due to a person breathing from the source video 300.

A signal 340 can be added to the intermediate video 330 to generate a modified video 350 in which the physiological measure can be extracted that has a value at or below the corresponding physiological measure threshold. The signal 340 can comprise, for example, fluctuations in average skin color corresponding to a heart rate below a heart rate threshold or fluctuations in shoulders and/or chest outlines indicating a respiratory rate below a respiratory rate threshold.

In some embodiments, the intermediate video 330 can be provided as the modified video, in which case the physiological measure typically cannot be extracted from the modified video. For example, fluctuations in the skin color of the person's face can be substantially absent from the modified video, or the chest or shoulders can be kept at substantially constant position in the modified video. However, addition of the signal 340 in the modified video 350 can provide the advantage that analysis of the modified video 350 can yield physiological measures indicating the person is a calm state, which can provide the person with, for example, advantages in business negotiations, as previously described. In addition, a modified video in which physiological measures can be extracted makes it less likely that a party analyzing the video for the presence of physiological cues will think that the source video has been processed to mask physiological cues. Supplying the intermediate video 330 to another party may tip off the receiving party that the source video has been processed if a heart rate, respiratory rate, or other physiological measures cannot be extracted from the supplied video.

FIG. 3B shows an exemplary masking of redness in a person's face. In FIG. 3B, a source video 355 comprises video of a person in which the redness of the person's face 360 exceeds a redness baseline 370 by more than a skin redness shift threshold 365. The redness of the person's face can be masked by applying a threshold filter 380 to the source video 355. The threshold filter 380 can modify the source video 355 such that the redness in a person's face is within the skin redness shift threshold of that person's redness baseline. In FIG. 3B, the threshold filter 380 has modified the source video 355 such that the redness of the person's face 385 in the modified video 387 is within the skin redness shift threshold 365 of the redness baseline 370. In various embodiments, the source video 355 can modified to bring the redness levels of the person's face down to levels indicating a calm emotional state by creating an interference pattern and then adding the interference pattern to the source video.

In various embodiments, reddening of a person's face can be determined by determining the difference in redness levels between regions in a person's face that typically turn redder as part of a person's emotional response, such as a person's cheeks, and a skin area that does not typically turn redder as part of a person's emotional response, such as a person's neck, nose or hands, rather than measuring the redness shift from a skin redness baseline. For example, the physiological cue that a person's face is turning red can be determined by analyzing whether the redness of a region of the person's cheek has shifted by more than the skin redness shift threshold from the redness of the tip of the person's nose or hands.

FIG. 3C shows an exemplary masking of physiological cues in source video 392 containing nervous tics—blinking 394 and twitching 396 of a corner of the mouth. Nervous tics are typically brief, and can be masked by, for example, passing the source video 392 through a low-pass filter 398 that attenuates signals that occur at, for example, 20 Hz and higher. In other embodiments, the low-pass filter can attenuate signals above other frequencies, such as 10 Hz, 15 Hz and 25 Hz. Typically, the low-pass filter 398 is a temporal filter. In some embodiments, the low-pass filter 398 can be applied to a limited spatial region of the source video 392, such as the region around the person's eyes to mask blinks, or to regions of the face other than the person's mouth so that a person's speech movements are not affected. For example, the low-pass filter 398 can be applied to the mouth corner regions to mask tics that occur at these locations while limiting the impact of low-pass filtering on general movement of the mouth related to speech. In FIG. 3C, the source video 392 is passed through a low-pass filter 398 to generate a modified video 399 in which the blinks 394 and twitches 396 at the corner of the person's mouth have been substantially removed, or at least attenuated. A low-pass filter can be used to mask other physiological cues that are brief in nature, such as involuntary micro expressions that appear on a person's face according to emotions experienced by the person. In other embodiments, twitches, tics and micro expressions can be determined using known motion processing techniques and source video can be modified by performing motion adjustment post-processing to remove twitches, tics and micro expressions from the source video.

In general, a low-pass filter can be applied to source video to mask physiological cues that are brief without having to detect these brief physiological cues. In embodiments where the presence of physiological cues are detected, the physiological cue threshold can be an absolute threshold (e.g., 120 bpm, 15 breaths per minute) or a relative threshold, such as a physiological measure exceeding an associated physiological cue baseline by, for example, 30%. A physiological cue baseline can be person-specific.

The physiological cue masking techniques described herein can be combined to mask multiple physiological cue types in a source video. For example, any combination of elevated heart rate, elevated respiratory rate, reddening of the face, the presence of nervous tics and micro expressions can be simultaneously masked from a source video. Accordingly, a source video can be passed through at least one of a low-pass filter for masking brief physiological cues, a threshold filter for masking redness, and other modules that remove physiological cues from a source video and insert signals into a modified video that yield a physiological measurement below an associated physiological measure threshold. In some embodiments, the source video is passed through a filter that substantially removes nervous tics or micro expressions lasting approximately 100 ms or less.

In some embodiments, the physiological cue masking can be configurable. For example, a person can select which physiological cues are to be masked from a source video and select physiological cue threshold values (e.g., heart rate threshold, respiratory rate threshold, skin redness shift threshold). A person can also configure which components of a source video are to be absent from the modified video (e.g., a person can indicate that skin color fluctuations due to the blood pulsation effect are to be absent from the modified video) and whether the modified video is to contain signals corresponding to physiological measurements that are below physiological cue thresholds (e.g. a person can indicate that the fluctuations skin color in the modified video corresponding to the blood pulsation that are not to exceed the heart rate threshold). In various embodiments, these configurations can be varied by a person dynamically. For example, a person can adjust heart rate and respiratory rate thresholds during a videoconference.

Accordingly, the masking of physiological cues can comprise removing a component of the source video from which a physiological measurement can be extracted for determining the presence of physiological cues, as well as injecting into the modified video a signal from which a physiological measure can be extracted that is below an associated physiological measure threshold. It is to be understood that a modified video in which a physiological cue has been masked can contain artifacts of the signal from which the presence of a physiological cue in the source video was determined. For example, a modified video may contain artifacts or remnants of skin color fluctuations in a source video. Any artifacts or remnants in the modified video are typically small enough in magnitude to prevent an associated physiological measurement or cue from being detected in the modified video.

Alternatively, any of the physiological measure thresholds described herein can be determined based on person observation. For example, a physiological cue masking system can determine physiological measure thresholds automatically by observing a person in a controlled environment, such as when the person is expected to be in a calm state (such as in a session dedicated to training a physiological cue masking system to establish physiological measure thresholds and/or baselines for a person) or by determining physiological measure thresholds and baselines from ordinary usage of a physiological cue masking system. For example, if a physiological cue masking system determines that a person's heart rate is typically between 70 and 80 bpm when using the system, it can establish a heart rate baseline of 70-80 bpm, and set a heart rate threshold that is 30% (or any other percentage) above the baseline.

Another physiological cue that can be masked using the technologies described herein is sweating, which can indicate that a person is distressed or anxious. The masking of sweating can comprise detecting that a person is sweating based on the identification of specular highlights on the person's face in the video, and modifying the source video by smoothing the identified regions to remove the spectral highlight. In some embodiments, the smoothing can be an averaging of the identified spectral highlight regions with nearby areas on the person's face where there are not spectral highlights.

In some embodiments, physiological cues can be masked by including compression artifacts in the modified video. These compression artifacts can be artificially generated and can mimic compression artifacts (such as ringing, mosquito noise and blocking) that arise from video compression techniques. In various embodiments, compression artifacts can be selectively applied to regions where a physiological cue has been detected. For example, if a computing device detects that a person in a video is sweating or twitching, compression artifacts can be applied locally to these regions. Alternatively, compression artifacts can be applied to the whole video or to the portion of the video occupied by a person's face to conceal physiological cues.

In some embodiments, the techniques described herein can generate modified video in which physiological cues have been introduced or in which extractable physiological measure have been increased. For example, modified video can be generated in which a person in the video can be determined to have an elevated heart or respiratory rate, have increased redness in the face, or be sweating. An elevated heart rate can be introduced in a modified video by, for example, adding a blood pulsation effect signal reflecting a heart rate greater than a heart rate threshold. The redness of a user's face can be increased by, for example, changing the color of pixels in the area of the user's face such that the skin redness exceeds a skin redness threshold by more than a skin redness shift threshold. Sweating can be added by adding specular reflections to the user's face. Being able to introduce physiological cues may be desirable when, for example, a first party in a videoconference wishes to deceive a second party to the videoconferencing into thinking that the first is nervous or anxious. This could be useful when the first party is negotiating with the second party.

Figure 4:
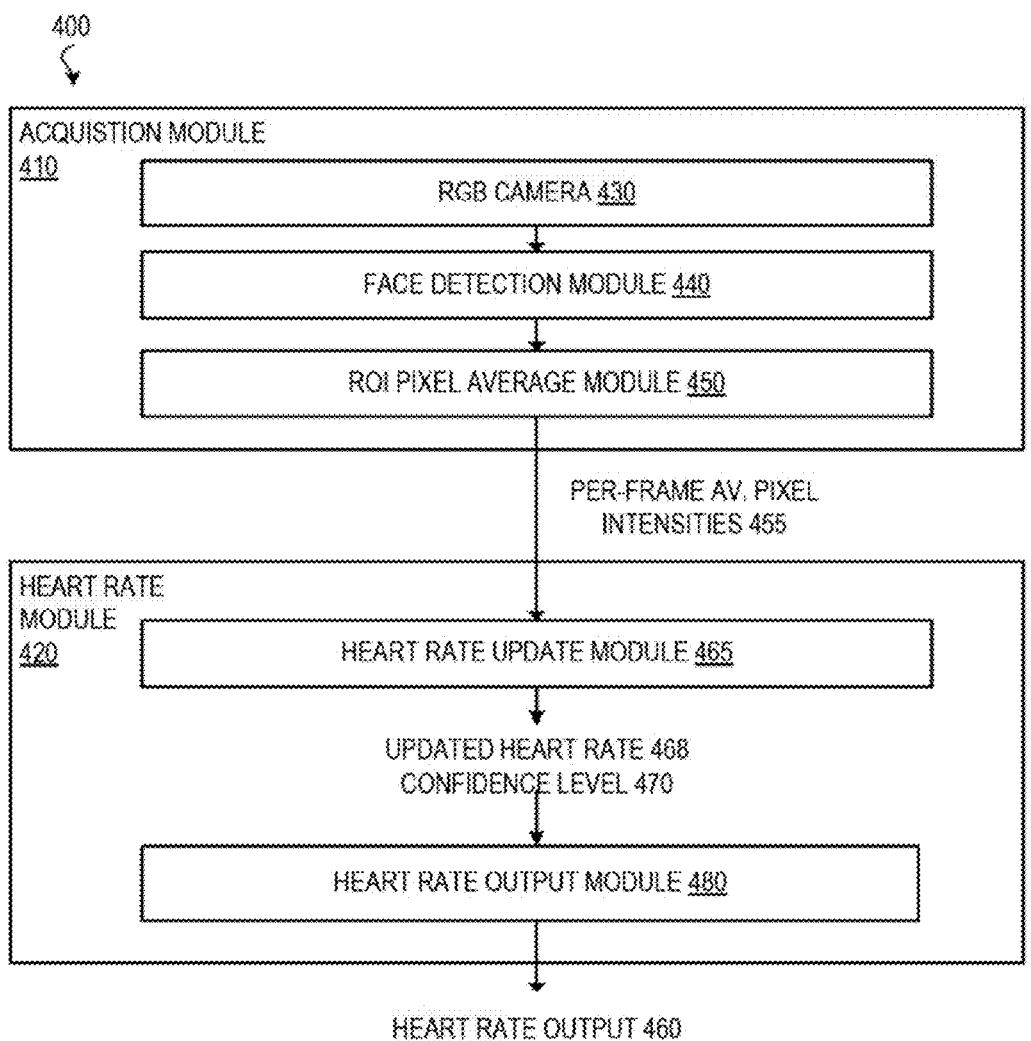
FIG. 4 is a block diagram of an exemplary system for determining a person's heart rate in a contactless manner based on video received from a single video source.

FIG. 4 is a block diagram of an exemplary system 400 for determining a person's heart rate in a contactless manner based on video received from a single video source. The system 400 comprises an acquisition module 410 and a heart rate module 420. The acquisition module 410 comprises an RGOB camera 430, a face detection module 440 to detect the face of one or more people in the video generated by the RGB camera 430, and an ROI (region of interest) pixel average module 450 to determine average pixel intensities 455 in ROI sin the detected faces for individual frames in the video.

The heart rate module 420 generates a heart rate output 460 from the per-frame average pixel intensities 455 generated by the acquisition module 410. A heart rate update module 465 determines an updated heart rate 468, and, optionally, a confidence level 470. The updated heart rate 468 can be based on pixel intensities generated from a window of frames comprising the current frame and the previous N frames covering at least the last two identifiable heart beats (typically, two to five seconds worth of frames). The window can be a sliding window such that pixel intensities for the oldest frame are shifted out of the window and pixel intensities for the latest frame are appended to the window when pixel intensities are generated for a current frame. Thus, although the updated heart rate 468 can be updated on a frame-by-frame basis, the update heart rate 468 is typically calculated using data from the current frame and the previous N frames.

The heart rate update module 465 can use various approaches to determine the updated heart rate 468, such as, for example, by selecting the heart rate in the color channel having the strongest periodicity as the updated heart rate for that frame. The heart rate update module 465 can also determine per-frame confidence levels 470, which can be a confidence level for each color channel. The confidence level can be calculated for each frame, and typically refers to the confidence level of the updated heart rate calculated from pixel intensity data generated from the current frame and the previous N frames. The confidence levels 470 can depend on various factors such as variations in pixel intensity peak magnitudes, variations in intervals between pixel intensity peaks in each color channel, and variations in periodicity in heart rate among the color channels.

A heart rate output module 480 determines the heart rate output 460 for a person being recorded by the RGB camera 430. The heart rate output module 480 can determine the heart rate output 460 by, for example, using the updated heart rate 468 for a frame if a confidence level 470 for that frame is above a certain level, or by averaging the updated heart rate 468 over the prior N frames.

Figure 5:
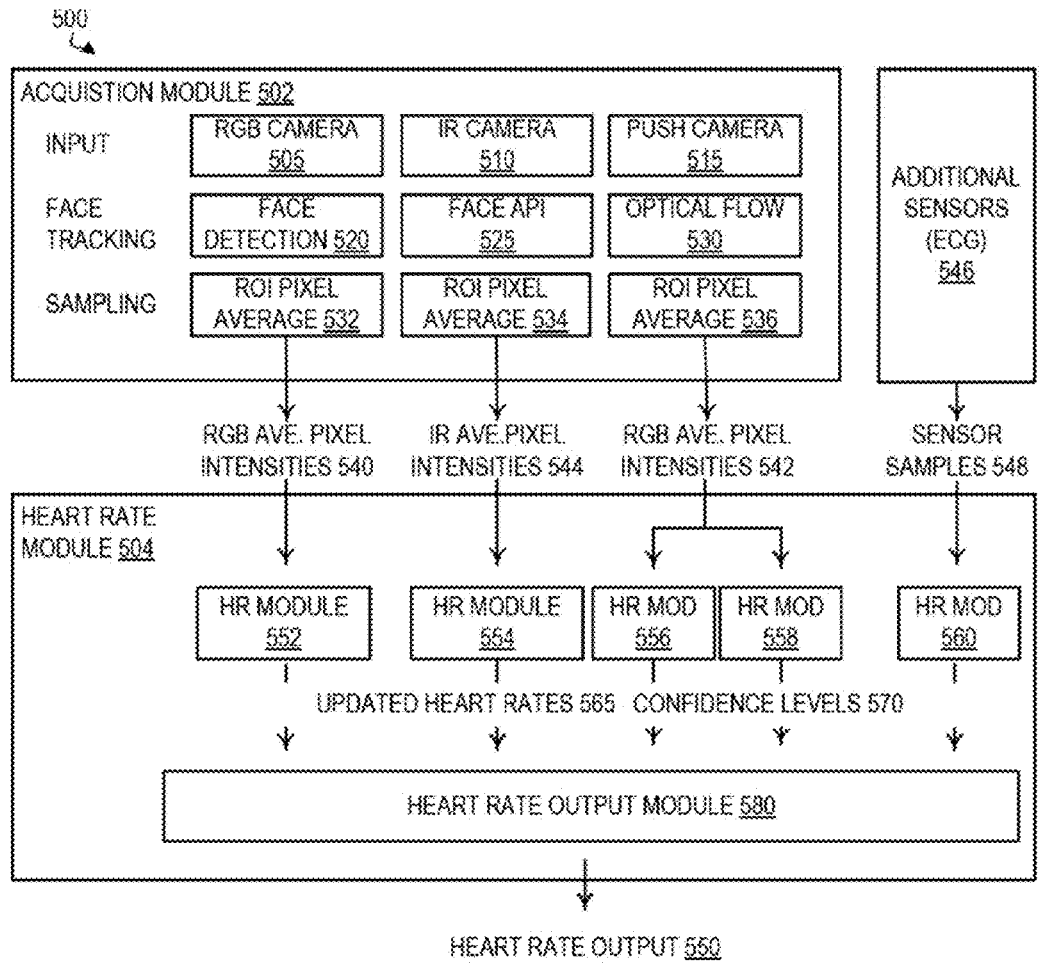
FIG. 5 is a block diagram of an exemplary system for determining a person's heart rate in a contactless manner based on video received from multiple sources.

FIG. 5 is a block diagram of an exemplary system 500 for determining a person's heart rate in a contactless manner based on video received from multiple sources—three video sources and additional sensors. The system 500 comprises an acquisition module 502 and a heart rate module 504. The acquisition module 502 comprises an RGB camera 505, an infrared (IR) camera 510, and a push camera 515 as video sources. Frame-to-frame face tracking is performed by a face detection module 520 (which can use, for example a Haar-based face detection technique), a module using the third-party face API facial recognition platform 525, and an optical flow-based tracking module 530. Although the specific face tracking approaches 520, 525, and 530 are shown as being paired with specific cameras 505, 510 and 515, any face tracking modules can be used with any video source, including face tracking modules not shown in FIG. 5. Pixel intensity sampling is performed by ROI pixel average modules 532, 534 and 536, which generate per-frame RGB average pixel intensities 540 and 542, and per-frame IR average pixel intensities 544. The system 500 further includes additional sensors 546, such as electrocardiogram (ECG) sensors, that generate sensor samples 548 that can be used in determining a person's heart rate.

The heart rate module 504 determines a heart rate output 550 from the per-frame pixel intensities 540, 542, 544 and sensor samples 548, which are provided to heart rate update modules 552, 554, 556, 558 and 560 that calculate the heart rates 565 for individual input channels (RGB camera, IR camera, additional sensors) on a frame-by-frame basis, based on a window comprising the current frame and the previous N frames. The heart rate modules can output updated heart rates 565 and confidence levels 570 in a similar manner as the updated heart rates 468 and confidence levels 470 are calculated, as described above in regards to FIG. 4. Multiple heart rate update modules can output an updated heart rate for a particular input. For example, heart rate modules 556 and 558 can calculate updated heart rates from the push camera video, with one of the modules calculating an updated heart rate for a larger ROI and the other updated heart rate module calculating a per-frame heart rate for a smaller ROI.

A heart rate output module 580 generates the heart rate output 550 from the updated heart rates 565 and confidence levels 570 generated by the heart rate update modules 552, 554, 556, 558 and 560. The heart rate output module 580 can determine the heart rate output 550 in various manners, such as by averaging the updated heart rates 565 from the prior N frames for inputs having a confidence level above a certain value, or using the heart rate that has the strongest periodicity or greatest peak magnitudes among the various input sources. The modules illustrated in the systems 400 and 500 can be implemented in hardware, software, firmware or any combination thereof.

The systems 400 and 500 can be used in physiological cue masking systems or devices that mask elevated heart rates. In some embodiments, a system having multiple input sources can have more or fewer input sources than those shown in FIG. 5. For example, a system could determine a person's heart rate only from video captured by a single RGB or IR camera. Although the systems 400 and 500 are discussed above in the context of determining a person's heart rate, the systems 400 and 500 can be extended to determine other physiological measures, such as respiratory rate and the redness of a person's race. Accordingly, other physiological measures can be determined from multiple input sources as well as single input sources.

Figure 6:
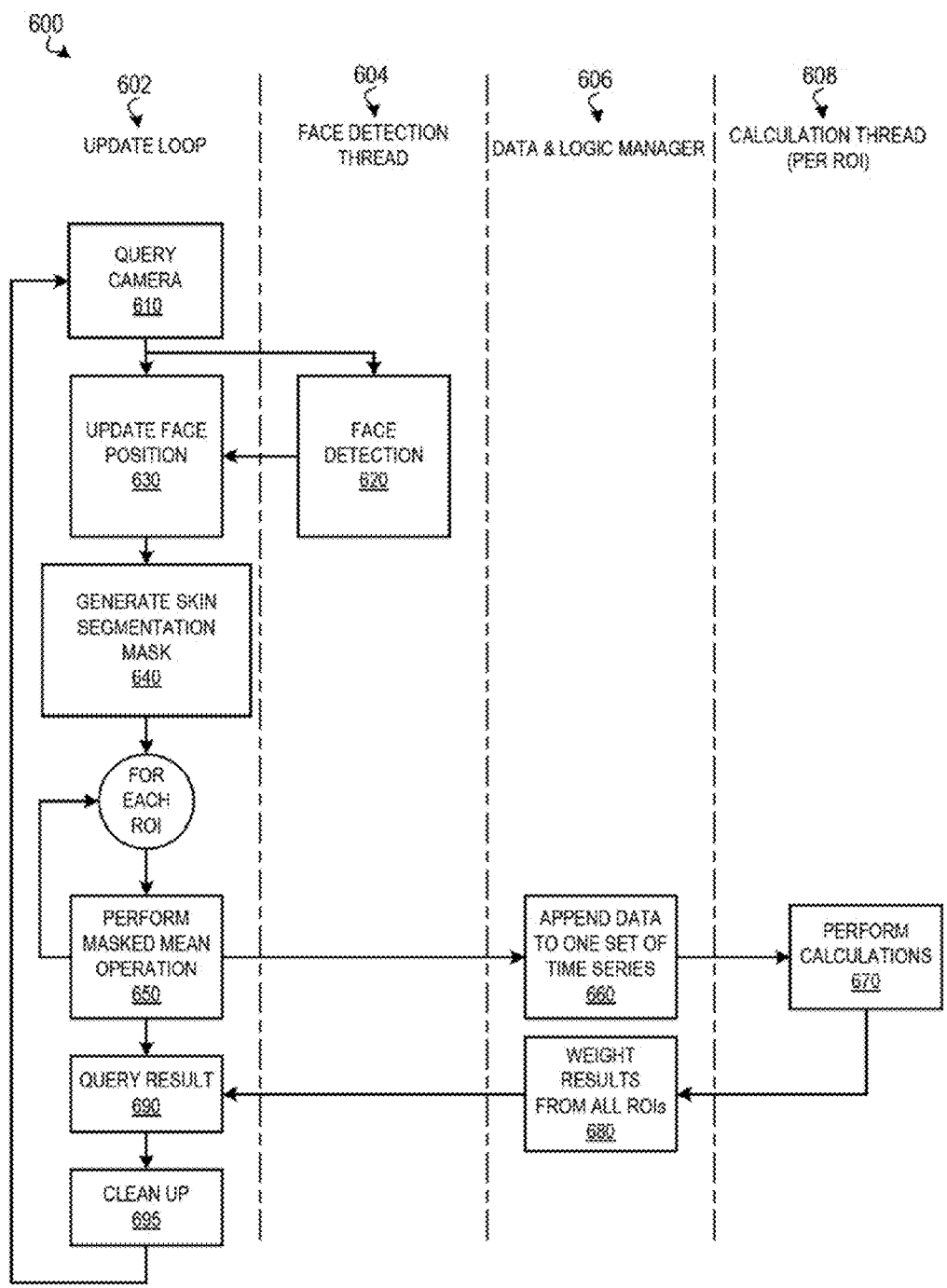
FIG. 6 is a flowchart of an exemplary method of determining a person's heart rate from video.

FIG. 6 is a flowchart of an exemplary method 600 of determining a person's heart rate from a video. The process acts of the method 600 belong to an update loop 602, a face detection thread 604, a data and logic manager 606 and a calculation thread 608. In the first process act in the update loop 602, process act 610, a camera is queried and pixel data for a video frame is returned. After the camera has provided data for a frame, a face detection process act 620 is performed in the face detection thread 604. At process act 630, the position of a person's face in the video is updated. At process act 640, a skin segmentation mask is generated and a masked mean operation is performed on pixel intensity values for each region of interest at process act 650. The data and logic manager 606 appends the averaged pixel intensity values to a set of time series (e.g., a set of frames) in the video at process act 660, and the calculation thread 608 calculates a heart rate value for each region of interest based on the appended average pixel intensity data at process act 670. The data and logic manager 606 then weights the heart rate values from the regions of interest at process act 680 to determine a heart rate for a person in the video, and the result is queried by the update loop 602 at process act 690. The update loop 602 then performs clean up at process act 695 and the update loop 602 returns to process act 610 to process another video frame.

Figure 7:
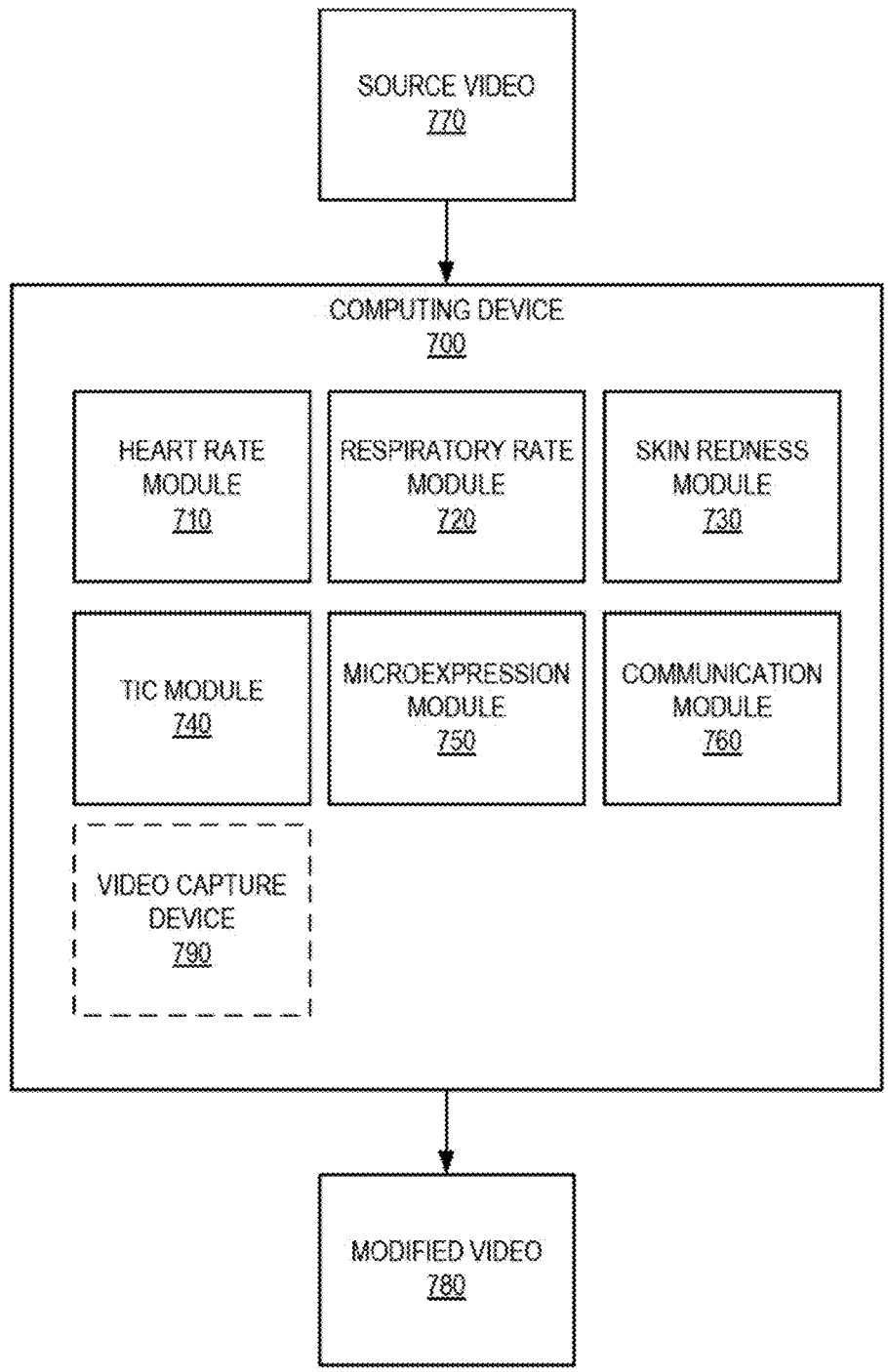
FIG. 7 is a block diagram of a first exemplary computing device in which technologies described herein can be implemented.

FIG. 7 is a block diagram of an exemplary computing device 700 in which technologies described herein can be implemented. The computing device 700 comprises a heart rate module 710, a respiratory rate module 720, a skin redness module 730, a tic module 740, a micro expression module 750 and a communication module 760. The computing device 700 can generate a modified video 770 from a source video 780 in which one or more physiological cues present in the source video 780 are substantially absent from the modified video 770.

The heart rate module 710 can determine a person's heart rate from fluctuations in average pixel intensities in regions of a person's face in the source video 770, determine that the heart rate is elevated, by determining that the heart rate exceeds a heart rate threshold, substantially remove the average pixel intensity fluctuations from the source video, and inject average pixel intensities fluctuations corresponding to a heart rate different from that indicated by the fluctuations in the source video. In some embodiments, the heart rate module 420 or 504 can be implemented as the heart rate module 710, and in other embodiments, the heart rate module 710 can be different from heart rate module 420 or 504. The respiratory rate module 720 can detect a person's respiratory rate from the source video 780, determine that the respiratory rate is elevated, by determining that the respiratory rate exceeds a respiratory rate threshold, and modify the source video 780 such that a respiratory rate cannot be or is at least difficult to extract from the modified video 770 based on the rise and fall of a person's chest, or that a respiratory rate equal to or less than a respiratory rate threshold can be extracted from the modified video 770.

The skin redness module 730 can determine the amount of shift in redness in a person's skin color and modify the source video 780 such that the redness shift is within a skin redness shift threshold of a baseline redness level. The tic module 740 and micro expression modules 750 can remove a person's tics and micro expressions from the source video 780. The communication module 760 can receive the source video 780 and can send the modified video 770 to another computing device. In some embodiments, the computing device 700 can comprise additional modules (shown in FIG. 7 with dashed lines), such as a video capture device 790, which can be any camera (e.g., RGB, IR, push) that provides source video to the computing device 700).

It is to be understood that FIG. 7 illustrates one example of a set of modules that can be included in a computing device. In other embodiments, a computing device can have more or fewer modules than those shown in FIG. 7. For instance, a physiological cue masking system that only masks elevated heart and respiratory rates may not comprise skin redness, tic and micro expression modules. Further, modules shown as separate in FIG. 7 can be combined into a single module, or a single module shown in FIG. 7 can be split into multiple modules. Moreover, any of the modules shown in FIG. 7 can be part of the operating system of the computing device 700, one or more software applications independent of the operating system, or operate at another software layer. In some embodiments, the computing device 700 can comprise an acquisition module that comprises the video capture device 790, a face detection module and an ROI pixel average module; and a heart rate module that comprises a per-frame heart rate module and a heart rate output module.

The modules shown in FIG. 7 can be implemented in software, hardware, firmware or combinations thereof. A computer device referred to as being programmed to perform a method can be programmed to perform the method via software, hardware, firmware or combinations thereof.

FIG. 8 is a block diagram of a first exemplary method 800 of masking physiological cues. The method 800 can be performed by, for example, a videoconferencing system installed in a conference room at a place of business that is being used by a business executive participating in negotiations with a remote party. The videoconferencing system comprises an RGB camera. At process act 810, a source video of at least one person comprising one or more physiological cue is received. In the example, the videoconferencing system receives video of the executive via the RGB camera. The executive is engaged in high-stakes negotiations that are not going well. The executive is nervous and worried, and his heart is racing. At process act 820, a modified video is generated in which at least one of the one or more physiological cues is masked. In the example, the videoconferencing system generates modified video that that masks the executive's heart rate. At process act 830, the modified video is sent to a second computing device. In the example, the videoconferencing system sends the modified video to the other party's videoconferencing system, which could be a desktop or laptop computer, a videoconferencing system installed in a conference room, or other computing device.

Figure 9:
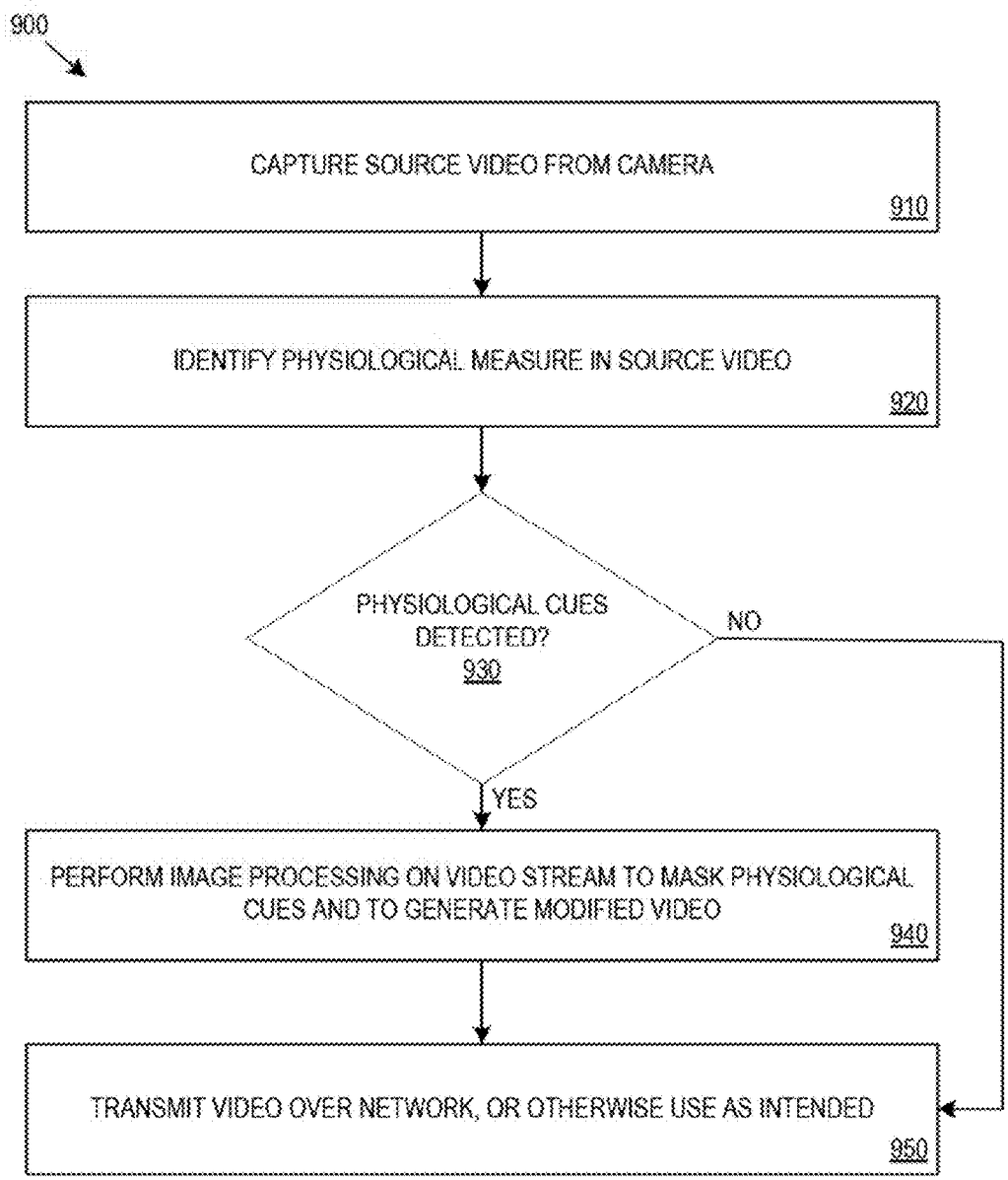
FIG. 9 is a flowchart of a second exemplary method of masking physiological cues.

FIG. 9 is a flowchart of a second exemplary method 900 of masking physiological cues. The method 900 can be performed by, for example, a desktop computer executing a VoIP (Voice over Internet Protocol) application having video capabilities and capable of masking physiological cues. The VoIP application person can be a business manager delivering a quarterly update to her team. During the update, one of the manager's employees gets into a heated discussion with the manager, and the manager's face turns red because she is upset. At process act 910, video is captured from a camera. In the example, source video is captured from a camera integrated into the manager's desktop computer. At process act 920, physiological measures are detected in the source video. In the example, a redness of a region of the manager's face is detected by analyzing pixel intensities in the source video. At process act 930, physiological cues, if any, are detected in the source video, based on the identified physiological measure. Detection of physiological cues can comprise detection of undesired physiological cues (e.g., twitches) or physiological measures that are outside of a specified range (e.g., a threshold value). In the example, the desktop computer determines that the redness of the manager's face exceeds a skin redness baseline associated with the manager by more than a skin redness shift threshold. At process act 940, image processing is performed on the video stream to mask the physiological cues. In the example, since reddening of the manager's face is the only physiological cue detected, the desktop computer performs image processing on the manager's face in the video to reduce the skin redness so that it is within the skin redness shift threshold of the manager's skin redness baseline. At process act 950, the modified video is sent over a network to another computing device or otherwise used as intended. In the example, the desktop computer sends the modified video to her team's computing devices. If no physiological cues are detected at process 930, the method proceeds to process act 950.

Figure 10:
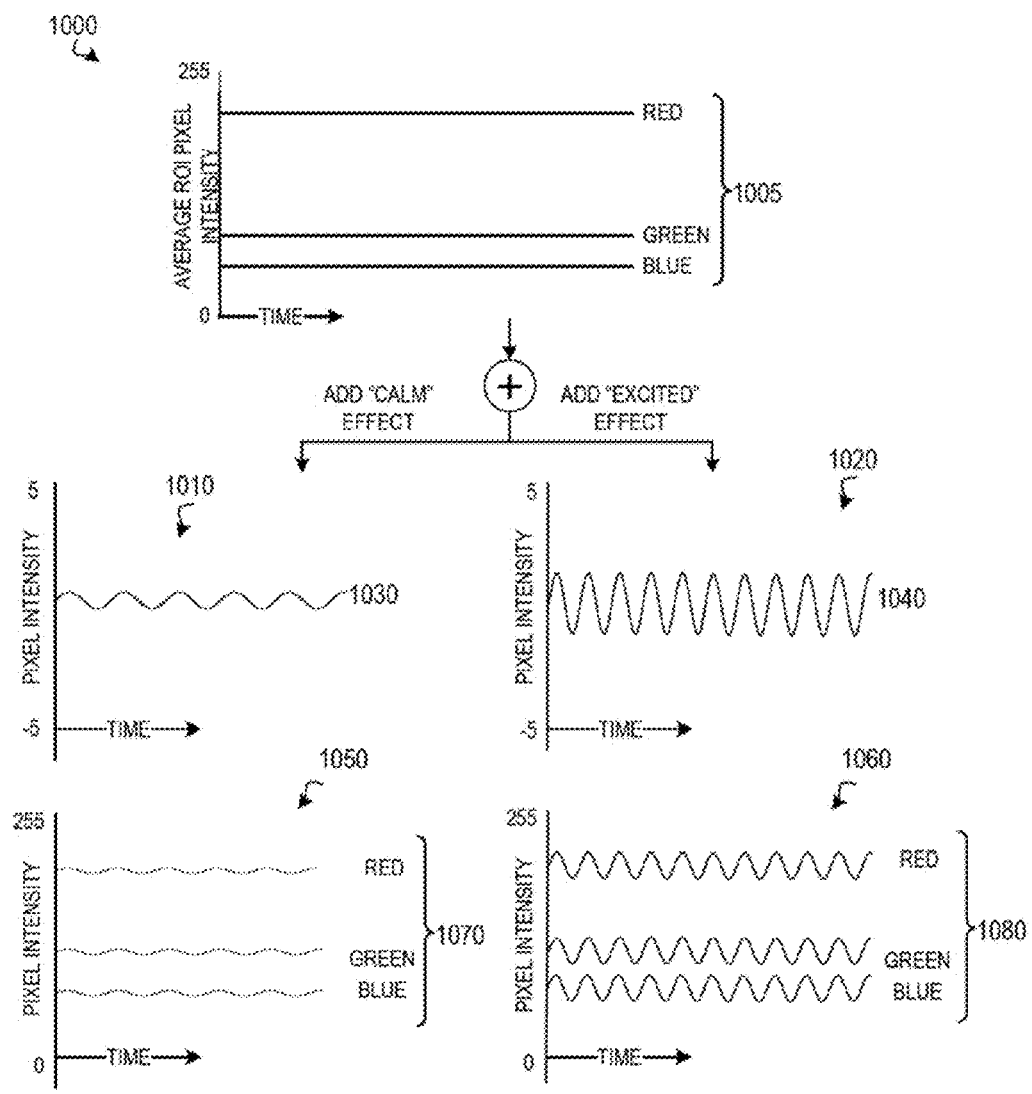
FIG. 10 illustrates exemplary signals that can be added to a computer graphics model of a human character to mimic the blood pulsation effect.

FIG. 10 illustrates exemplary signals that can be added to a computer graphics model (e.g., a computer graphics imaging (CGI) model) of a human character to mimic the blood pulsation effect. Generally, pixel intensity values in the skin of a CGI character presented at a display can comprise a combination of static model textures and lighting scenarios. An additional texture can be added to human skin texture networks that vary over time (e.g., sinusoidally) to add the blood pulsation effect to the CGI character. In some embodiments, the frequency of the sinusoid is between about 0.7 to 3.0 Hz to represent a range of heart rates (42-180 bpm) corresponding to a range of emotional states to be exhibited by the CGI character. The amplitude of the sinusoid can be varied by color, luma and/or chrominance channel.

Graph 1000 shows exemplary average pixel intensities 1005 for a region of interest of a CGI character in video employing an RGB color scheme. The average pixel intensities 1005 are for a CGI character in which the pulsation effect is not modeled. Therefore, the pixel intensities are unvarying over time. Graphs 1010 and 1020 show exemplary blood pulsation effect signals 1030 and 1040 that can be added to the pixel intensity values 1005 to indicate calm and exited states of the CGI character, respectively. The excited blood pulsation effect signal 1040 has an increased frequency as well as increased amplitude relative to the calm blood pulsation effect signal 1030, although, in some embodiments, the amplitude of an excited blood pulsation effect signal can be substantially similar to that of a calm blood pulsation effect signal. Typically, blood pulsation effect signals have low amplitudes relative to the average pixel intensity values captured by a camera. Although the blood pulsation effect signals 1030 and 1040 are shown in FIG. 10 as sinusoidal signals, they can be any type of periodic or aperiodic signal.

If the CGI character is in an environment in which the character would typically be considered to be in a calm emotional state (e.g., walking in a park, having a casual conversation with another CGI character), a blood pulsation effect signal having a frequency of 1.0-1.3 Hz (reflecting a heart rate of 60-80 bpm) could be added to the character. If the CGI character is an environment in which the character would be typically considered to be excited (e.g., in a gunfight), a 2.0-2.5 Hz signal (reflecting a heart rate of 120-150 bpm) could be added. In some embodiments, blood pulsation effect signals can comprise variations (random or otherwise) in the amplitude of pixel intensity peaks and valleys to provide a more accurate modeling of the pulsation effect. Small variations in the time between pixel intensity peaks and valleys could also be introduced into blood pulsation effect signals. In addition to being used to add skin color fluctuations to the face of a CGI character, the blood pulsation effect signals described in regards to FIG. 10 can be injected into a modified video generated by a physiological cue masking system. That is, the blood pulsation effect signals discussed in regard to FIG. 10 could comprise the signal 340 added to the intermediate video 330 to generate the modified video 350 in FIG. 3. Inclusion of a blood pulsation effect signal with variations in pixel intensity peak amplitude and frequency can make it less likely that a party receiving the modified video would conclude that the source video has been modified to mask physiological cues.

Computer-readable instructions that add blood pulsation effects to CGI characters can be incorporated into CGI modeling suites, provided as a plugin to CGI modeling suites, or made available to persons or computing devices in other manners.

FIG. 1 is a flowchart of an exemplary method 100) of adding a blood pulsation effect to a computer graphics model of a human character. The method 1100 can be performed by, for example, a cloud-based gaming service hosting a massively multiplayer online game. At process act 1110, a computer graphics model of a human character comprising a face region is received. In the example, a rendering engine of the cloud-based gaming service receives a computer graphics model of a human character. At process act 1120, a skin texture comprising a blood pulsation effect is added to the face region. In the example, the rendering engine adds a skin texture comprising a blood pulsation effect to the facial region of the character.

The following scenarios illustrate exemplary advantages of the technologies described herein. In a first exemplary usage scenario, a physiological cue masking system can be used to aid people participating in videoconferences. For example, consider a CEO participating in videoconference-based negotiations who is nervous because he is in a weak bargaining position. His heart is racing, but he wants to appear calm to the other videoconference participants. Even though other parties to the videoconference will likely not be able to notice the CEO's increased heart rate, the CEO is concerned that the other parties may performing computer analysis of the video in an attempt to detect and monitor his heart rate. The physiological cue masking system can detect the blood pulsation effect in his face and adjusts the skin color in his face to remove the blood pulsation effect. The masking system can then inject a blood pulsation effect signal into the video that indicates the CEO has a heart rate indicating a calm emotional state. Any party to the videoconferencing negotiations that happens to be analyzing the video to determine the CEO's heart rate may detect a heart rate that indicates the CEO is in a calm state. Thus, technologies described herein can act as a countermeasure to attempts by parties to a videoconference to perform analysis on a video to determine a person's emotional state by extracting their heart rate, respiratory rate, skin redness, etc. from the video.

In a second exemplary usage scenario, in a live television broadcast, a physiological cue masking system can be used to mask physiological cues in video of presentations given by public speakers. For example, consider a politician who is addressing his constituents regarding the state of the economy in a live television broadcast. The status of the economy is dire, the politician is nervous, and the politician has a facial twitch at the corner of her mouth that manifests itself when she is nervous. The physiological cue masking system can analyze motion in the video, detect when there are facial twitches and remove them from the video. In the modified video observed by the viewers, the politician's twitches are absent, making it less likely that the viewers can tell that the politician is nervous.

In yet another embodiment, technologies described herein can be used to add skin color fluctuations to the skin texture of a CGI character to mimic the blood pulsation effect. Adding this physiological effect to CGI characters is one method that may narrow the "uncanny valley," the effect of viewers to view with repulsion CGI characters that look and act almost, but not quite perfectly, like actual human beings. The frequency of this blood pulsation effect can be predetermined or person-configurable. In addition, the added heart rate frequency can be determined based on the CGI character's environment.

In additional usage scenarios, the technologies described herein can be used to monitor a person's emotional response to content output at an output device and take an action depending on the person's emotional response to the content. For example, a computing device can display an advertisement for a particular good or service and analyze video of a viewer's response to the advertisement to detect a viewer's emotional response to the advertisement. A promotion can be provided to the viewer based on their response to the advertisement. For instance, if a person is streaming a movie or other media) from a cloud-based video streaming service, the computing device can detect whether the viewer's heart rate and/or respiratory rate increases while an advertisement is being played before or during the movie. In response, the computing device can send a message to the cloud-based service, indicating the viewer's emotional response and the service can cause a promotion to be sent to the person. The promotion can be, for example, a coupon sent to an email account of the viewer or via an SMS or MMS message sent to a phone number associated with the viewer. The cloud-based service can also send additional advertisements for good or services related to the goods or service in the advertisement to which the viewer had an excited emotional response.

In another usage example, detection of a viewer's excited emotional state in response to content presented at a computing device can determine what content is next presented at the computing device. For instance, if a computing device determines that a person displayed an excited emotional response to a particular movie scene, song or video game sequence, a similar movie scene, song or video game sequence can be next presented at the output device. Alternatively, in some embodiments, detection of an excited response by a person in response to content displayed at an output device can cause a system to not display (or display less) additional content having characteristics similar to content that caused the excited emotional response. For example, if a person watching a horror movie provided by a cloud-based video streaming service has more than a set number of excited responses while watching a horror movie, the service can select or suggest a movie that is less scary for the person to watch next.

The technologies, techniques and embodiments described herein can be performed by any of a variety of computing devices, including mobile devices (such as smartphones, handheld computers, tablet computers, laptop computers, media players, portable gaming consoles, cameras and video recorders), non-mobile devices (such as desktop computers, servers, stationary gaming consoles, smart televisions) and embedded devices (such as devices incorporated into a vehicle). As used herein, the term "computing devices" includes computing systems and includes devices comprising multiple discrete physical components.

Figure 12:
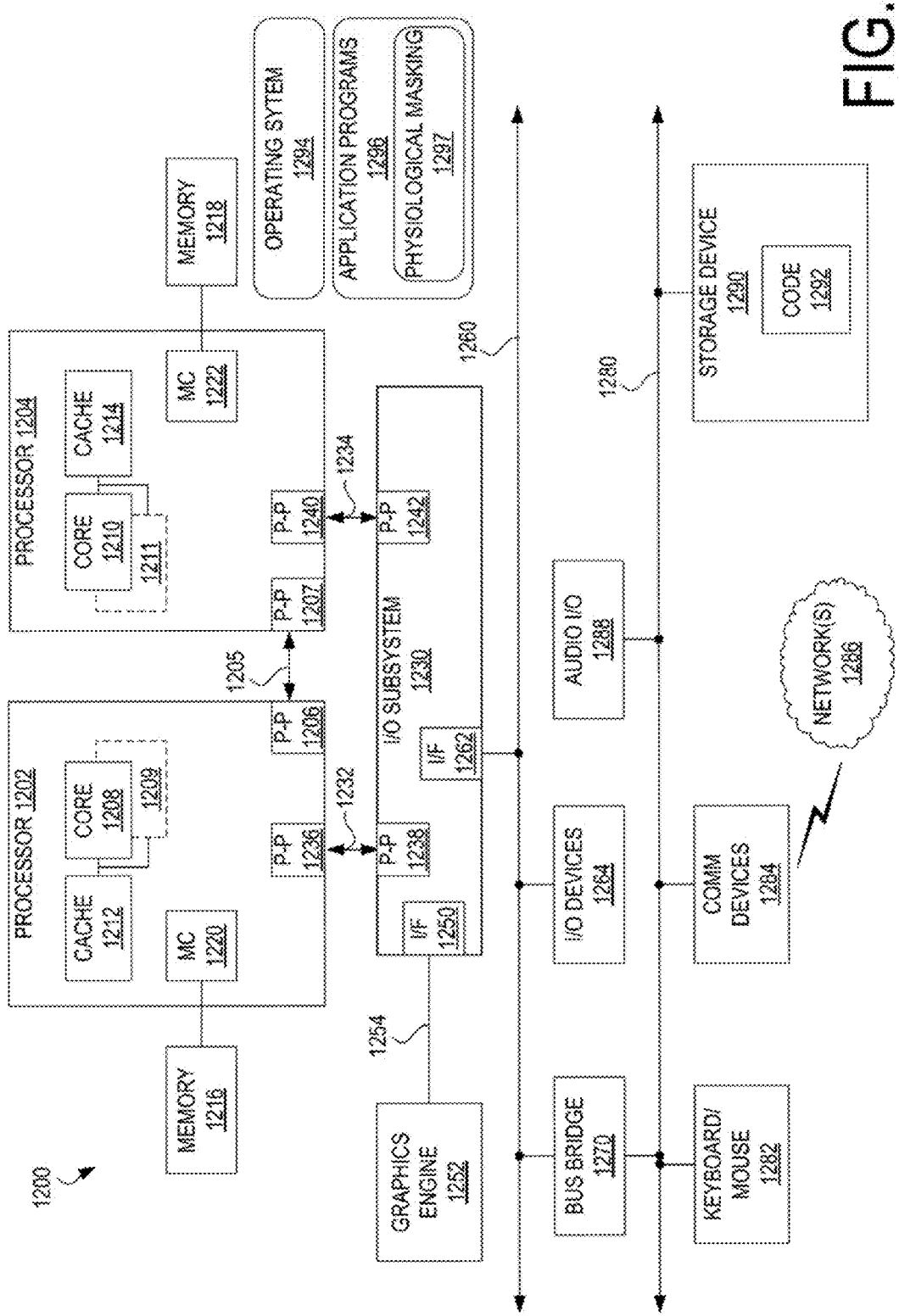
FIG. 12 is a block diagram of a second exemplary computing device in which technologies described herein can be implemented.

FIG. 12 is a block diagram of a second exemplary computing device 1200 in which technologies described herein can be implemented. Generally, components shown in FIG. 12 can communicate with other shown components, although not all connections are shown, for ease of illustration. The device 1200 is a multiprocessor system comprising a first processor 1202 and a second processor 1204 and is illustrated as comprising point-to-point (P-P) interconnects. For example, a point-to-point (P-P) interface 1206 of the processor 1202 is coupled to a point-to-point interface 1207 of the processor 1204 via a point-to-point interconnection 1205. It is to be understood that any or all of the point-to-point interconnects illustrated in FIG. 12 can be alternatively implemented as a multi-drop bus, and that any or all buses illustrated in FIG. 12 could be replaced by point-to-point interconnects.

As shown in FIG. 12, the processors 1202 and 1204 are multicore processors. Processor 1202 comprises processor cores 1208 and 1209, and processor 1204 comprises processor cores 1210 and 1211. Processor cores 1208-1211 can execute computer-executable instructions in a manner similar to that discussed below in connection with FIG. 13, or in other manners.

Processors 1202 and 1204 further comprise at least one shared cache memory 1212 and 1214, respectively. The shared caches 1212 and 1214 can store data (e.g., instructions) utilized by one or more components of the processor, such as the processor cores 1208-1209 and 1210-1211. The shared caches 1212 and 1214 can be part of a memory hierarchy for the device 1200. For example, the shared cache 1212 can locally store data that is also stored in a memory 1216 to allow for faster access to the data by components of the processor 1202. In some embodiments, the shared caches 1212 and 1214 can comprise multiple cache layers, such as level 1 (L1), level 2 (L2), level 3 (L3), level 4 (L4), and/or other caches or cache layers, such as a last level cache (LLC).

Although the device 1200 is shown with two processors, the device 1200 can comprise only one processor or more than two processors. Further, a processor can comprise one or more processor cores. A processor can take various forms such as a central processing unit, a controller, a graphics processor, an accelerator (such as a graphics accelerator or digital signal processor (DSP)) or a field programmable gate array (FPGA). A processor in a device can be the same as or different from other processors in the device. In some embodiments, the device 1200 can comprise one or more processors that are heterogeneous or asymmetric to a first processor, accelerator, FPGA, or any other processor. There can be a variety of differences between the processing elements in a system in terms of a spectrum of metrics of merit including architectural, micro architectural, thermal, power consumption characteristics and the like. These differences can effectively manifest themselves as asymmetry and heterogeneity amongst the processors in a system. In some embodiments, the processors 1202 and 1204 reside in the same die package.

Processors 1202 and 1204 further comprise memory controller logic (MC) 1220 and 1222. As shown in FIG. 12, MCs 1220 and 1222 control memories 1216 and 1218 coupled to the processors 1202 and 1204, respectively. The memories 1216 and 1218 can comprise various types of memories, such as volatile memory (e.g., dynamic random access memories (DRAM), static random access memory (SRAM)) or non-volatile memory (e.g. flash memory). While MCs 1220 and 1222 are illustrated as being integrated into the processors 1202 and 1204, in alternative embodiments, the MCs can be logic external to a processor, and can comprise one or more layers of a memory hierarchy.

Processors 1202 and 1204 are coupled to an Input/Output (10) subsystem 1230 via P-P interconnections 1232 and 1234. The point-to-point interconnection 1232 connects a point-to-point interface 1236 of the processor 1202 with a point-to-point interface 1238 of the I/O subsystem 1230, and the point-to-point interconnection 1234 connects a point-to-point interface 1240 of the processor 1204 with a point-to-point interface 1242 of the I/O subsystem 1230. Input/Output subsystem 1230 further includes an interface 1250 to couple I/O subsystem 1230 to a graphics engine 1252, which can be a high-performance graphics engine. The I/O subsystem 1230 and the graphics engine 1252 are coupled via a bus 1254. Alternately, the bus 1244 could be a point-to-point interconnection.

Input/Output subsystem 1230 is further coupled to a first bus 1260 via an interface 1262. The first bus 1260 can be a Peripheral Component Interconnect (PCI) bus, a PCI Express bus, another third generation I/O interconnection bus or any other type of bus.

Various I/O devices 1264 can be coupled to the first bus 1260. A bus bridge 1270 can couple the first bus 1260 to a second bus 1280. In some embodiments, the second bus 1280 can be a low pin count (LPC) bus. Various devices can be coupled to the second bus 1280 including, for example, a keyboard/mouse 1282, audio I/O devices 1288 and a storage device 1290, such as a hard disk drive, solid-state drive or other storage device for storing computer-executable instructions (code) 1292. The code 1292 comprises computer-executable instructions for performing technologies described herein. Additional components that can be coupled to the second bus 1280 include communication device(s) 1284, which can provide for communication between the device 1200 and one or more wired or wireless networks 1286 (e.g. Wi-Fi, cellular or satellite networks) via one or more wired or wireless communication links (e.g., wire, cable, Ethernet connection, radio-frequency (RF) channel, infrared channel, Wi-Fi channel) using one or more communication standards (e.g., IEEE 802.11 standard and its supplements).

The device 1200 can comprise removable memory such as flash memory cards (e.g., SD (Secure Digital) cards), memory sticks, Subscriber Identity Module (SIM) cards). The memory in device 1200 (including caches 1212 and 1214, memories 1216 and 1218 and storage device 1290) can store data and/or computer-executable instructions for executing an operating system 1294 and application programs 1296. Example data includes web pages, text messages, images, sound files, video data, physiological measure thresholds for particular persons or other data sets to be sent to and/or received from one or more network servers or other devices by the device 1200 via one or more wired or wireless networks, or for use by the device 1200. The device 1200 can also have access to external memory (not shown) such as external hard drives or cloud-based storage.

The operating system 1294 can control the allocation and usage of the components illustrated in FIG. 12 and support one or more application programs 1296. The application programs 1290 can include common mobile computing device applications (e.g., email applications, calendars, contact managers, web browsers, messaging applications) as well as other computing applications, such as a physiological cue masking application 1297 that can generate modified video from source video received by the device 1200 in which physiological cues present in the source video are substantially absent from the modified video.

The device 1200 can support various input devices, such as a touch screen, microphone, camera, physical keyboard, proximity sensor and trackball, and one or more output devices, such as a speaker and a display. Other possible input and output devices include piezoelectric and other haptic I/O devices. Any of the input or output devices can be internal to, external to or removably attachable with the device 1200. External input and output devices can communicate with the device 1200 via wired or wireless connections.

In addition, the computing device 1200 can provide one or more natural person interfaces (NUIs). For example, the operating system 1292 or applications 1294 can comprise speech recognition logic as part of a voice person interface that allows a person to operate the device 1200 via voice commands. Further, the device 1200 can comprise input devices and logic that allows a person to interact with the device 1200 via a body, hand or face gestures. For example, a person's hand gestures can be detected and interpreted to provide input to a gaming application.

The device 1200 can further comprise one or more wireless modems (which could comprise communication devices 1284) coupled to one or more antennas to support communication between the system 1200) and external devices. The wireless modems can support various wireless communication protocols and technologies such as Near Field Communication (NFC), Wi-Fi, Bluetooth, 4G Long Term Evolution (LTE), Code Division Multiplexing Access (CDMA), Universal Mobile Telecommunication System (UMTS) and Global System for Mobile Telecommunication (GSM). In addition, the wireless modems can support communication with one or more cellular networks for data and voice communications within a single cellular network, between cellular networks, or between the mobile computing device and a public switched telephone network (PSTN).

The device 1200 can further include at least one input/output port (which can be, for example, a USB port, IEEE 1394 (FireWire) port, and/or RS-232 port) comprising physical connectors, a power supply, a satellite navigation system receiver such as a GPS receiver, a gyroscope, an accelerometer and a compass. A GPS receiver can be coupled to a GPS antenna. The device 1200 can further include one or more additional antennas coupled to one or more additional receivers, transmitters and/or transceivers to enable additional functions.

It is to be understood that FIG. 12 illustrates one exemplary computing device architecture. Computing devices based on alternative architectures can be used to implement technologies described herein. For example, instead of the processors 1202 and 1204, and the graphics engine 1252 being located on discrete integrated circuits, a computing device can comprise a SoC (system-on-a-chip) integrated circuit incorporating multiple processors, a graphics engine and additional components. Further, a computing device can connect elements via bus configurations different from that shown in FIG. 12. Moreover, the illustrated components in FIG. 12 are not required or all-inclusive, as shown components can be removed and other components added in alternative embodiments.

Figure 13:
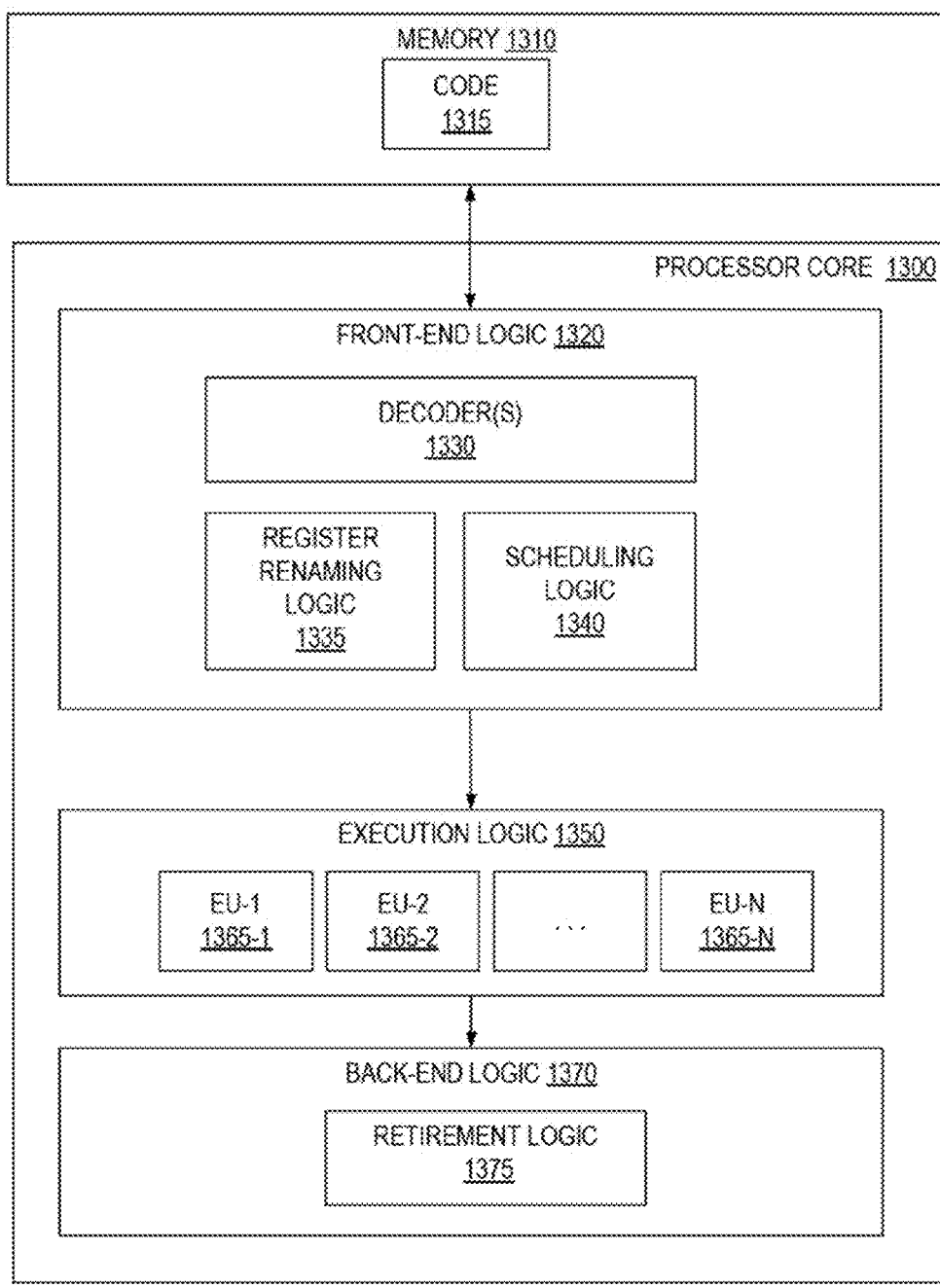
FIG. 13 is a block diagram of an exemplary processor core to execute computer-executable instructions for implementing technologies described herein.

FIG. 13 is a block diagram of an exemplary processor core 1300 to execute computer-executable instructions for implementing technologies described herein. The processor core 1300 can be a core for any type of processor, such as a microprocessor, an embedded processor, a digital signal processor (DSP) or a network processor. The processor core 1300 can be a single-threaded core or a multithreaded core in that it can include more than one hardware thread context (or "logical processor") per core.

FIG. 13 also illustrates a memory 1310 coupled to the processor 1300. The memory 1310 can be any memory described herein or any other memory known to those of skill in the art. The memory 1310 can store computer-executable instruction 1315 (code) executable by the processor core 1300.

The processor core comprises front-end logic 1320 that receives instructions from the memory 1310. An instruction can be processed by one or more decoders 1330. The decoder 1330 can generate as its output a micro operation such as a fixed width micro operation in a predefined format, or generate other instructions, micro instructions, or control signals, which reflect the original code instruction. The front-end logic 1320 further comprises register renaming logic 1335 and scheduling logic 1340, which generally allocate resources and queues operations corresponding to converting an instruction for execution.

The processor core 1300 further comprises execution logic 1350, which comprises one or more execution units (EUs) 1365-1 through 1365-N. Some processor core embodiments can include a number of execution units dedicated to specific functions or sets of functions. Other embodiments can include only one execution unit or one execution unit that can perform a particular function. The execution logic 1350 performs the operations specified by code instructions. After completion of execution of the operations specified by the code instructions, back-end logic 1370 retires instructions using retirement logic 1375. In some embodiments, the processor core 1300 allows out of order execution but requires in-order retirement of instructions. Retirement logic 1370 can take a variety of forms as known to those of skill in the art (e.g. re-order buffers or the like).

The processor core 1300 is transformed during execution of instructions, at least in terms of the output generated by the decoder 1330, hardware registers and tables utilized by the register renaming logic 1335, and any registers (not shown) modified by the execution logic 1350. Although not illustrated in FIG. 13, a processor can include other elements on an integrated chip with the processor core 1300. For example, a processor can include additional elements such as memory control logic, one or more graphics engines, I/O control logic and/or one or more caches.

Referring back to FIG. 1, the network or cloud 180 can provide various cloud-based services that can be used to implement technologies described herein. For example, the masking of physiological cues can be performed by cloud-based services. For instance, the first computing device 140 can send the source video 120 to a cloud-based service that masks elevated heart and respiratory rates for the person 130, and sends the modified video 160 to the second computing device 170. In some embodiments, cloud-based services can add a blood pulsation effect to the face of computer graphics models of human characters provided by the first computing device.

Any of the disclosed methods can be implemented as computer-executable instructions or a computer program product. Such instructions can cause a computer to perform any of the disclosed methods. Generally, as used herein, the term "computer" refers to any computing device or system described or mentioned herein, or any other computing device. Thus, the term "computer-executable instruction" refers to instructions that can be executed by any computing device described or mentioned herein, or any other computing device.

The computer-executable instructions or computer program products as well as any data created and used during implementation of the disclosed technologies can be stored on one or more tangible computer-readable storage media, such as optical media discs (e.g., DVDs. CDs), volatile memory components (e.g., DRAM, SRAM), or non-volatile memory components (e.g., flash memory, disk drives). Computer-readable storage media can be contained in computer-readable storage devices such as solid-state drives, USB flash drives, and memory modules. Alternatively, the computer-executable instructions can be performed by specific hardware components that contain hardwired logic for performing all or a portion of disclosed methods, or by any combination of computer-readable storage media and hardware components.

The computer-executable instructions can be part of, for example, a dedicated software application or a software application that is accessed via a web browser or other software application (such as a remote computing application). Such software can be executed, for example, on a single computing device or in a network environment using one or more network computers. Further, it is to be understood that the disclosed technology is not limited to any specific computer language or program. For instance, the disclosed technologies can be implemented by software written in C++, Java. Perl, JavaScript, Adobe Flash, or any other suitable programming language. Likewise, the disclosed technologies are not limited to any particular computer or type of hardware. Certain details of suitable computers and hardware are known and need not be set forth in detail in this disclosure.

Furthermore, any of the software-based embodiments (comprising, for example, computer-executable instructions for causing a computer to perform any of the disclosed methods) can be uploaded, downloaded or remotely accessed through a suitable communication means. Such suitable communication means include, for example, the Internet, the World Wide Web, an intranet, cable (including fiber optic cable), magnetic communications, electromagnetic communications (including RF, microwave, and infrared communications), electronic communications, or other such communication means.

As used in this application and in the claims, a list of items joined by the term "and/or" can mean any combination of the listed items. For example, the phrase "A, B and/or C" can mean A; B; C; A and B; A and C; B and C; or A, B and C. As used in this application and in the claims, a list of items joined by the term "at least one of" can mean any combination of the listed terms. For example, the phrases "at least one of A, B or C" can mean A; B; C; A and B; A and C; B and C; or A, B and C.

The disclosed methods, apparatuses and systems are not be construed as limiting in any way. Instead, the present disclosure is directed toward all novel and nonobvious features and aspects of the various disclosed embodiments, alone and in various combinations and subcombinations with one another. The disclosed methods, apparatuses, and systems are not limited to any specific aspect or feature or combination thereof, nor do the disclosed embodiments require that any one or more specific advantages be present or problems be solved.

Theories of operation, scientific principles or other theoretical descriptions presented herein in reference to the apparatuses or methods of this disclosure have been provided for the purposes of better understanding and are not intended to be limiting in scope. The apparatuses and methods in the appended claims are not limited to those apparatuses and methods that function in the manner described by such theories of operation.

Although the operations of some of the disclosed methods are described in a particular, sequential order for convenient presentation, it is to be understood that this manner of description encompasses rearrangement, unless a particular ordering is required by specific language set forth herein. For example, operations described sequentially can in some cases be rearranged or performed concurrently. Moreover, for the sake of simplicity, the attached figures may not show the various ways in which the disclosed methods can be used in conjunction with other methods.

The following examples pertain to further embodiments.

Example 1

A method of masking physiological cues, the method comprising: receiving source video of at least one person, the source video comprising one or more physiological cues; generating modified video in which at least one of the one or more physiological cues is masked; and sending the modified video to a second computing device.

Example 2

The method of Example 1, the method further comprising detecting at least one of the one or more physiological cues in the source video.

Example 3

The method of Example 2, wherein the detecting comprises: determining a physiological measure of the person from the source video; and determining that the physiological measure exceeds a physiological measure threshold.

Example 4

The method of Example 3, wherein the modified video has the characteristic that the physiological measure as determined from the modified video is different from the physiological measure as determined from the source video.

Example 5

The method of Example 3, wherein the modified video has the characteristic that the physiological measure as determined from the modified video is less than or equal to the physiological measure as determined from the source video.

Example 6

The method of Example 3, wherein the physiological measure is a heart rate, the physiological measure threshold is a heart rate threshold, and the detecting comprises determining the heart rate based at least in part on fluctuations in average pixel intensities in one or more regions of the person's face in the source video.

Example 7

The method of Example 6, wherein fluctuations in average pixel intensities in the one or more regions of the person's face in the modified video fluctuate at a different rate than the heart rate determined from the source video.

Example 8

The method of Example 6, wherein fluctuations in average pixel intensities in the one or more regions of the person's face in the modified video fluctuate at a rate below the heart rate threshold.

Example 9

The method of Example 6, wherein the fluctuations in average pixel intensities in the one or more regions of the person's face in the source video are substantially absent from the modified video.

Example 10

The method of Example 3, wherein the physiological measure is a respiratory rate, the physiological measure threshold is a respiratory rate threshold, and the detecting comprises determining the respiratory rate of the person based on a rate at which the chest and/or shoulders of the person rise and fall in the source video.

Example 11

The method of Example 10, wherein a rate at which the shoulder and/or chest of the person rise and fall in the modified video is different from the rate at which the shoulders and/or chest of the person rise and fall in the source video.

Example 12

The method of Example 10, wherein the shoulders and chest of the person do not substantially rise or fall in the modified video.

Example 13

The method of any of Examples 2-12, wherein the detecting comprises: determining a skin redness of the person based at least in part on pixel intensities in one or more regions of the person's face in the source video: and determining that the skin redness exceeds a skin redness baseline by more than a skin redness shift threshold.

Example 14

The method of Example 13, wherein a skin redness in the one or more regions of the person's face in the modified video is different than the skin redness determined from the source video.

Example 15

The method of Example 13, wherein a skin redness in the one or more regions of the person's face in the modified video is within the skin redness shift threshold of the skin redness baseline.

Example 16

The method of any of Examples 2-12, wherein the detecting comprises identifying specular reflections in one or more regions of the person's face in the source video, the generating the modified video comprising smoothing the one or more regions of the person's face to at least reduce the intensity of the identified specular reflections.

Example 17

The method of any of Examples 1-12, wherein the generating the modified video comprises substantially removing nervous tics and/or micro expressions from the source video.

Example 18

The method of any of Examples 1-12, wherein the generating the modified video comprises passing the source video through a filter that substantially removes nervous tics or micro expressions lasting approximately 100 ms or less.

Example 19

One or more computer-readable storage media storing computer-executable instructions for causing a computing device to perform any one of the methods of Examples 1-18.

Example 20

One or more computing devices programmed to perform of any one of the methods of Examples 1-18.

Example 21

A method comprising sending computer-executable instructions to one or more computing devices to cause the one or more computing devices to perform a method, the method comprising: receiving source video of at least one person, the source video comprising one or more physiological cues; generating modified video in which at least one of the one or more physiological cues is masked; and sending the modified video to a second computing device; and storing the computer-executable instructions at the one or more computing devices.

Example 22

One or more computing devices comprising: a communication module to receive source video of a person and to send modified video of the person to a second computing device, the source video comprising one or more physiological cues, at least one of the physiological cues being substantially absent from the modified video; and a heart rate module to determine a heart rate of the person based at least in part on fluctuations in average pixel intensities in one or more regions of the person's face in the source video, to determine that the heart rate exceeds a heart rate threshold, to remove the fluctuations from the source video, and to insert fluctuations in average pixel intensities in the one or more regions of the person's fact in the modified video that correspond to a heart rate equal to or less than the heart rate threshold.

Example 23

The one or more computing devices of Example 22, comprising at least one the following: a respiratory rate module to detect a respiratory rate of the person based at least in part on a rate at which the person's shoulders and/or chest are detected to rise and fall in the source video, to determine that the rise and fall rate of the persons' shoulders and/or chest exceeds a respiratory rate threshold, to substantially remove the rise and fall of the chest and/or shoulders from the source video, and to insert in the modified video the shoulders and/or chest rising and falling at a rate below the respiratory rate threshold; a skin redness module to determine a skin redness shift in one or more regions of the person's skin, to determine that the skin redness shift exceeds a skin redness baseline by more than a skin redness shift threshold, and to reduce the skin redness shift in the one or more regions of the person's skin such that the skin redness shift is within the skin redness shift threshold of the skin redness baseline; a tic module to remove tics present in one or more regions of the person's face in the source video from the modified video: and a micro expression module to remove micro expressions from the person's face in the source video from the modified video.

Example 24

One or more computer-readable media storing computer-executable instructions for causing a computing device to perform a method, the method comprising: receiving a computer graphics model of a human character, the computer graphics model comprising a face region; and adding a skin texture comprising a blood pulsation effect to the face region.

Example 25

The one or more computer-readable media of Example 24, the method further comprising determining an emotional state to be exhibited by the human character, the frequency of the blood pulsation effect in the skin texture being based at least in part on the emotional state.

Example 26

A method of adding a blood pulsation effect to a computer graphics model of a human character, the method comprising: receiving a computer graphics model of a human character, the computer graphics model comprising a face region; and adding a skin texture comprising a blood pulsation effect to the face region.

Example 27

One or more computing devices programmed to perform of a method of adding a blood pulsation effect to a computer graphics model of a human character, the method comprising: receiving a computer graphics model of a human character, the computer graphics model comprising a face region, and adding a skin texture comprising a blood pulsation effect to the face region.

Example 28

The one or more computing devices of Example 27, the method further comprising determining an emotional state to be exhibited by the human character, the frequency of the blood pulsation effect in the skin texture being based at least in part on the emotional state.

Example 29

A method of delivering a promotion to a person, the method comprising: sending media to a computing device, the media comprising an advertisement for a good or service; receiving an indication that a person exhibited an increased heart rate or increased respiratory rate in response to viewing the advertisement; and sending a message to the person comprising a promotion related to the good or service.

Example 30

A method of delivering a promotion to a person, the method comprising: sending media to a computing device, the media comprising an advertisement for a first good or service; receiving an indication that a person exhibited an increased heart rate or increased respiratory rate in response to viewing the advertisement; and sending additional media comprising an advertisement for a second good or service related to the first good or service.

Example 31

The method of Example 1, wherein the modified video comprises one or more compression artifacts.

Example 32

The method of Example 31, wherein the one or more compression artifacts are located in one or more regions of the video where the one or more physiological cues are located.

Example 33

The method of Example 3, wherein the modified video has the characteristic that the physiological measure as determined from the modified video is greater than the physiological measure as determined from the source video.

Example 34

The method of Example 6, wherein fluctuations in average pixel intensities in the one or more regions of the person's face in the modified video fluctuate at a rate above the heart rate threshold.

Example 35

The method of Example 13, wherein a skin redness in the one or more regions of the person's face in the modified video exceeds the skin redness shift threshold of the skin redness baseline.

Example 36

A method of masking physiological cues, the method comprising: receiving source video of at least one person, the source video comprising one or more physiological cues; generating modified video in which at least one of the one or more physiological cues is masked; and sending the modified video to a second computing device.

We claim:
1. One or more non-transitory computer-readable storage media storing computer-executable instructions for causing a computing device to perform a method of masking physiological cues, the method comprising:
   receiving source video of at least one person, the source video comprising one or more physiological cues;
   determining a physiological measure of the person from the source video;
   determining whether the physiological measure satisfies a predefined threshold indicative of one or more of the physiological cues;
   generating, in response to a determination that the physiological measure determined from the source video satisfies the predefined threshold, modified video in which at least one of the one or more physiological cues is masked; and
   sending the modified video to a second computing device.

2. The one or more non-transitory computer-readable storage media of claim 1, wherein the physiological measure is a heart rate, the physiological measure threshold is a heart rate threshold, and the detecting comprises determining the heart rate based at least in part on fluctuations in average pixel intensities in one or more regions of the person's face in the source video.

3. The one or more non-transitory computer-readable storage media of claim 2, wherein fluctuations in average pixel intensities in the one or more regions of the person's face in the modified video fluctuate at a different rate than the heart rate determined from the source video.

4. The one or more non-transitory computer-readable storage media of claim 2, wherein fluctuations in average pixel intensities in the one or more regions of the person's face in the modified video fluctuate at a rate below the heart rate threshold.

5. The one or more computer-readable storage media of claim 1, wherein the physiological measure is a respiratory rate, the physiological measure threshold is a respiratory rate threshold, and the detecting comprises determining the respiratory rate of the person based on a rate at which the chest and/or shoulders of the person rise and fall in the source video.

6. The one or more computer-readable storage media of claim 5, wherein a rate at which the shoulder and/or chest of the person rise and fall in the modified video is different from the rate at which the shoulders and/or chest of the person rise and fall in the source video.

7. The one or more computer-readable storage media of claim 5, wherein the shoulders and chest of the person do not substantially rise or fall in the modified video.

8. The one or more computer-readable storage media of claim 1, wherein the detecting comprises:
determining a skin redness of the person based at least in part on pixel intensities in one or more regions of the person's face in the source video; and
determining that the skin redness exceeds a skin redness baseline by more than a skin redness shift threshold.

9. The one or more computer-readable storage media of claim 8, wherein a skin redness in the one or more regions of the person's face in the modified video is different than the skin redness determined from the source video.

10. The one or more computer-readable storage media of claim 8, wherein a skin redness in the one or more regions of the person's face in the modified video is within the skin redness shift threshold of the skin redness baseline.

11. The one or more computer-readable storage media of claim 1, wherein the detecting comprises identifying specular reflections in one or more regions of the person's face in the source video, the generating the modified video comprising smoothing the one or more regions of the person's face to at least reduce the intensity of the identified specular reflections.

12. The one or more non-transitory computer-readable storage media of claim 1, wherein the generating the modified video comprises substantially removing nervous tics and/or microexpressions from the source video.

13. The one or more non-transitory computer-readable storage media of claim 1, wherein the generating the modified video comprises passing the source video through a filter that substantially removes nervous tics or microexpressions lasting approximately 100 ms or less.

14. The one or more non-transitory computer-readable storage media of claim 1, wherein generating the modified video comprises to:

generate an intermediate video by removing a component of the source video, wherein the component is indicative of the physiological measure; and
add a signal to the intermediate video, wherein the signal is indicative of a physiological measure that does not satisfy the predefined threshold.

15. The one or more non-transitory computer-readable storage media of claim 1, wherein generating the modified video comprises to smooth one or more specular highlights on the skin of a person in the source video.

16. The one or more non-transitory computer-readable storage media of claim 1, wherein generating the modified video comprises to add one or more compression artifacts to the source video.

17. A method of masking physiological cues, the method comprising:
receiving source video of at least one person, the source video comprising one or more physiological cues;
determining a physiological measure of the person from the source video;
determining whether the physiological measure satisfies a predefined threshold indicative of one or more of the physiological cues;
generating, in response to a determination that the physiological measure satisfies the predefined threshold determined from the source video, modified video in which at least one of the one or more physiological cues is masked; and
sending the modified video to a second computing device.

18. A method comprising:
sending computer-executable instructions to one or more computing devices to cause the one or more computing devices to perform a method, the method comprising:
receiving source video of at least one person, the source video comprising one or more physiological cues;
determining a physiological measure of the person from the source video;
determining whether the physiological measure satisfies a predefined threshold indicative of one or more of the physiological cues;
generating, in response to a determination that the physiological measure determined from the source video satisfies the predefined threshold, modified video in which at least one of the one or more physiological cues is masked;
sending the modified video to a second computing device; and
storing the computer-executable instructions at the one or more computing devices.

19. One or more computing devices programmed to perform a method, the method comprising:
receiving source video of at least one person, the source video comprising one or more physiological cues;
determining a physiological measure of the person from the source video;
determining whether the physiological measure satisfies a predefined threshold indicative of one or more of the physiological cues;
generating, in response to a determination that the physiological measure determined from the source video satisfies the predefined threshold, modified video in which at least one of the one or more physiological cues is masked; and
sending the modified video to a second computing device.

20. The one or more computing devices of claim 19, wherein the modified video has the characteristic that the physiological measure as determined from the modified video is different from the physiological measure as determined from the source video.

21. The one or more computing devices of claim 19, wherein the physiological measure is a heart rate, the physiological measure threshold is a heart rate threshold, and the detecting comprises determining the heart rate based at least in part on fluctuations in average pixel intensities in one or more regions of the person's face in the source video.

22. The one or more computing devices of claim 21, wherein fluctuations in average pixel intensities in the one or more regions of the person's face in the modified video fluctuate at a different rate than the heart rate determined from the source video.

23. The one or more computing devices of claim 21, wherein fluctuations in average pixel intensities in the one or more regions of the person's face in the modified video fluctuate at a rate below the heart rate threshold.

24. The one or more computing devices of claim 21, wherein the fluctuations in average pixel intensities in the one or more regions of the person's face in the source video are substantially absent from the modified video.

\* \* \* \* \*